(12) United States Patent
Kolios et al.

(10) Patent No.: US 11,691,115 B2
(45) Date of Patent: Jul. 4, 2023

(54) METHOD AND DEVICE FOR CARRYING OUT ENDOTHERMIC GAS PHASE-SOLID OR GAS-SOLID REACTIONS

(71) Applicant: BASF SE, Ludwigshafen am Rhein (DE)

(72) Inventors: Grigorios Kolios, Ludwigshafen (DE);
Bernd Zoels, Ludwigshafen (DE);
Matthias Kern, Ludwigshafen (DE);
Jens Bernnat, Ludwigshafen (DE);
Rene Koenig, Ludwigshafen (DE);
Friedrich Glenk, Ludwigshafen (DE);
Achim Wechsung, Ludwigshafen (DE)

(73) Assignee: BASF SE, Ludwigshafen am Rhein (DE)

( * ) Notice: Subject to any disclaimer, the term of this patent is extended or adjusted under 35 U.S.C. 154(b) by 721 days.

(21) Appl. No.: 16/346,672

(22) PCT Filed: Oct. 26, 2017

(86) PCT No.: PCT/EP2017/077433
§ 371 (c)(1),
(2) Date: May 1, 2019

(87) PCT Pub. No.: WO2018/083002
PCT Pub. Date: May 11, 2018

(65) Prior Publication Data
US 2020/0061565 A1  Feb. 27, 2020

(30) Foreign Application Priority Data
Nov. 4, 2016 (EP) ..................................... 16197338

(51) Int. Cl.
B01J 8/04 (2006.01)
B01J 38/32 (2006.01)
(Continued)

(52) U.S. Cl.
CPC ............... B01J 8/04 (2013.01); B01J 8/0492 (2013.01); B01J 8/0496 (2013.01); B01J 38/32 (2013.01);
(Continued)

(58) Field of Classification Search
CPC ..... C01B 2203/0811; C01B 2203/0844; C01B 2203/142; C01B 3/46; C01B 2203/0805;
(Continued)

(56) References Cited

U.S. PATENT DOCUMENTS 2,319,679 A    5/1943  Hasche et al.
2,557,143 A    6/1951  Royster
(Continued)

FOREIGN PATENT DOCUMENTS

WO    WO 2013/004398 A2    1/2013
WO    WO 2014/090914 A1    6/2014
WO    WO 2014/095661 A1    6/2014

OTHER PUBLICATIONS

International Search Report dated Feb. 22, 2018 in PCT/EP2017/077433 (with English translation), 5 pages
(Continued)

Primary Examiner — Imran Akram
(74) Attorney, Agent, or Firm — Grüneberg and Myers, PLLC

(57) ABSTRACT

The present invention relates to a process for conducting endothermic gas phase or gas-solid reactions, wherein the endothermic reaction is conducted in a production phase in a first reactor zone, the production zone, which is at least partly filled with solid particles, where the solid particles are in the form of a fixed bed, of a moving bed and in sections/or in the form of a fluidized bed, and the product-containing gas stream is drawn off from the production zone in the region of the highest temperature level plus/minus 200 K
(Continued)

and the product-containing gas stream is guided through a second reactor zone, the heat recycling zone, which at least partly comprises a fixed bed, where the heat from the product-containing gas stream is stored in the fixed bed, and, in the subsequent purge step, a purge gas is guided through the production zone and the heat recycling zone in the same flow direction, and, in a heating zone disposed between the production zone and the heat recycling zone, the heat required for the endothermic reaction is introduced into the product-containing gas stream and into the purge stream or into the purge stream, and then, in a regeneration phase, a gas is passed through the two reactor zones in the reverse flow direction and the production zone is heated up; the present invention further relates to a structured reactor comprising three zones, a production zone containing solid particles, a heating zone and a heat recycling zone containing a fixed bed, wherein the solid particles and the fixed bed consist of different materials.

15 Claims, 15 Drawing Sheets

(51) Int. Cl.
| | | |
|---|---|---|
| | *C01B 3/56* | (2006.01) |
| | *C01B 32/05* | (2017.01) |
| | *C01B 3/04* | (2006.01) |
| | *C01B 3/26* | (2006.01) |
| | *C01B 3/38* | (2006.01) |
| | *C01B 13/02* | (2006.01) |
| | *C04B 2/10* | (2006.01) |
| | *C07C 5/333* | (2006.01) |

(52) U.S. Cl.
CPC ............ *C01B 3/045* (2013.01); *C01B 3/26* (2013.01); *C01B 3/38* (2013.01); *C01B 13/0207* (2013.01); *C01B 32/05* (2017.08); *C04B 2/108* (2013.01); *C07C 5/3337* (2013.01); *B01J 2208/00522* (2013.01); *B01J 2219/0004* (2013.01); *C01B 3/56* (2013.01); *C01B 2203/043* (2013.01)

(58) Field of Classification Search
CPC ........ C01B 2203/0866; C01B 2203/82; C01B 3/28; C01B 3/30; C01B 2203/043; B01J 8/0496; B01J 2208/00522; B01J 8/0453; B01J 8/0492; B01J 2208/00513; B01J 2208/0053; B01J 2219/00117; B01J 8/0438; B01J 8/0457; B01J 2208/00309; B01J 2219/0004; B01J 38/32; B01J 8/06
See application file for complete search history.

(56) References Cited

U.S. PATENT DOCUMENTS

| | | | |
|---|---|---|---|
| 2,815,198 A | 12/1957 | Harris | |
| 4,240,805 A | 12/1980 | Sederquist | |
| 4,372,377 A | 2/1983 | Morris | |
| 6,331,283 B1 | 12/2001 | Roy et al. | |
| 7,943,808 B2 | 5/2011 | Hershkowitz et al. | |
| 2002/0007594 A1 | 1/2002 | Muradov | |
| 2003/0235529 A1 | 12/2003 | Hershkowitz et al. | |
| 2004/0170559 A1* | 9/2004 | Hershkowitz | C01B 3/38 423/655 |
| 2007/0003478 A1 | 1/2007 | Becker et al. | |
| 2007/0033873 A1* | 2/2007 | D'Souza | B01J 8/0496 48/127.9 |
| 2008/0142409 A1* | 6/2008 | Sankaranarayanan | B01J 19/2485 208/62 |
| 2009/0223371 A1* | 9/2009 | Nakao | B01D 53/047 96/130 |
| 2010/0081852 A1* | 4/2010 | Louret | B01J 8/0453 585/312 |
| 2010/0181539 A1* | 7/2010 | Apanel | C10K 1/002 252/373 |
| 2012/0256133 A1* | 10/2012 | Apanel | C10K 1/004 252/373 |
| 2014/0127121 A1* | 5/2014 | Maass | C01B 3/28 423/445 R |
| 2015/0044120 A1* | 2/2015 | Singh | C01C 1/0405 422/148 |
| 2015/0126627 A1* | 5/2015 | Apanel | C01B 3/44 422/141 |

OTHER PUBLICATIONS

International Preliminary Report on Patentability and Written Opinion of the International Searching Authority dated May 7, 2019 in PCT/EP2017/077433 filed Oct. 26, 2017 (with English translation), 13 pages.
European Search Report dated May 11, 2017 in Patent Application No. 16197338.3 (with English translation of categories of cited documents), 4 pages.
Octave Levenspiel, "Chemical Engineering's Grand Adventure" Chemical Engineering Science, vol. 43, No. 7, 1988, pp. 1427-1435.
Sang Bum Han, et al., "Water Splitting for Hydrogen Production with Ferrites" Solar Energy, vol. 81, 2007, pp. 623-628.
U.S. Appl. No. 15/574,692, filed Nov. 16, 2017, US 2018/0134629 A1, Grigorios Kolios, et al.
U.S. Appl. No. 15/779,596, filed May 29, 2018, US 2018/0273380 A1, Hans-Jürgen Maass, et al.

* cited by examiner

1: Production bed
2: Regenerator bed
3: Heating zone
4: Mixing/combustion chamber
5: Introduction of the carrier
6: Emptying of the solid product
7: Hot gas filter
8: Additional heating in the production bed
9: Additional heating in the regenerator bed
10: Phase separator/dedusting 1: Production bed
2: Regenerator bed
3: Heating zone
4: Mixing/combustion chamber
5: Introduction of the carrier
6: Emptying of the solid product
7: Hot gas filter
8: Additional heating in the production bed
9: Additional heating in the regenerator bed
10: Phase separator/dedusting

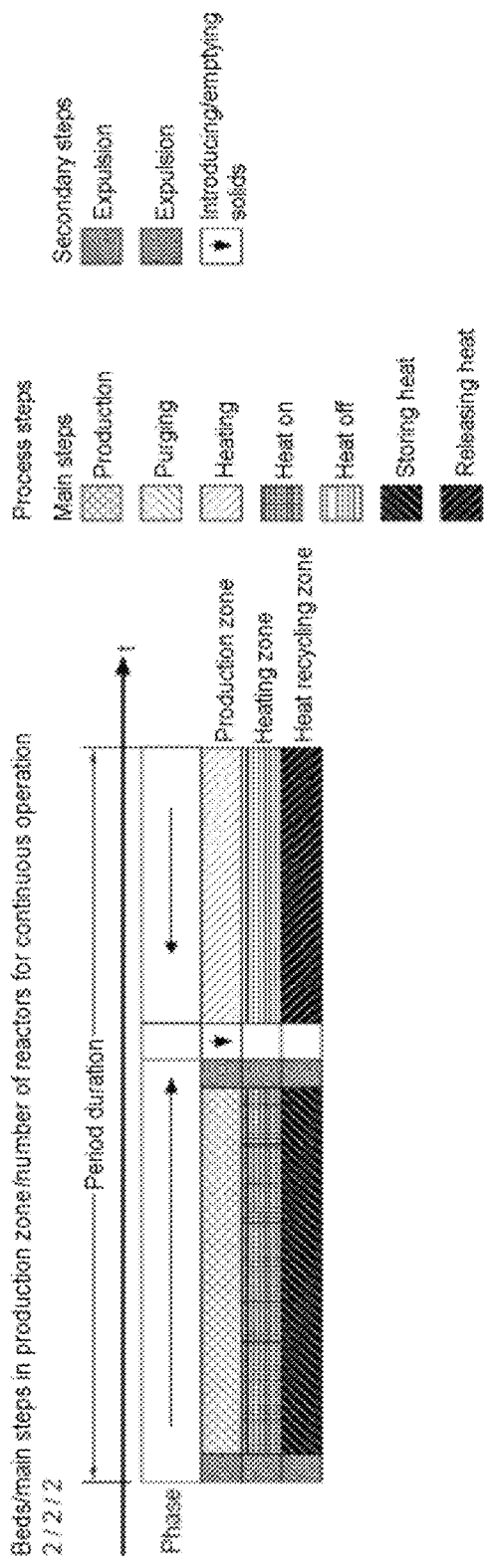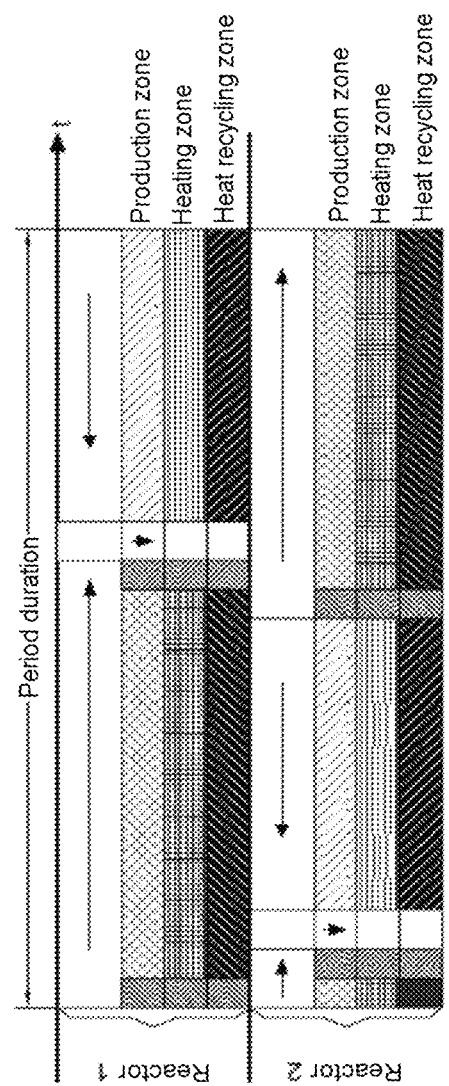
Figure 6 b
Figure 6 c

METHOD AND DEVICE FOR CARRYING OUT ENDOTHERMIC GAS PHASE-SOLID OR GAS-SOLID REACTIONS

The present invention relates to a process for conducting endothermic gas phase or gas-solid reactions, wherein the endothermic reaction is conducted in a production phase in a first reactor zone, the production zone, which is at least partly filled with solid particles, where the solid particles are in the form of a fixed bed, of a moving bed and in sections/or in the form of a fluidized bed, and the product-containing gas stream is drawn off from the production zone in the region of the highest temperature level plus/minus 200 K and the product-containing gas stream is guided through a second reactor zone, the heat recovery zone, which at least partly comprises a fixed bed, where the heat from the product-containing gas stream is stored in the fixed bed, and, in the subsequent purge step, a purge gas is guided through the production zone and the heat recovery zone in the same flow direction, and, in a heating zone disposed between the production zone and the heat recovery zone, the heat required for the endothermic reaction is introduced into the product-containing gas stream and into the purge stream or into the purge stream, and then, in a regeneration phase, a gas is passed through the two reactor zones in the reverse flow direction and the production zone is heated up. The present invention further relates to a structured reactor and to the use thereof.

Endothermic reactions are frequently at the start of the value creation chain of the chemical industry, for example in the cracking of mineral oil fractions, the reforming of natural gas or naphtha, the dehydrogenation of propane, the dehydroaromatization of methane to benzene, the reverse Boudouard reaction, coal gasification or the pyrolysis of hydrocarbons. In these reactions, temperatures between 500° C. and 1700° C. are required to achieve yields of industrial and economic interest. The main reason for this lies in the thermodynamic limitation of the equilibrium conversion. The provision of the heat of reaction required at this temperature level constitutes a great technical challenge.

According to the prior art, fluidized bed reactors are used for heat-integrated conduction of endothermic processes (Levenspiel, O. (1988), Chemical engineering's grand adventure. Chemical Engineering Science, 43(7), 1427-1435). Essentially four concepts are employed for the supply of heat to the endothermic reaction.

The prior art (cf. Fluidization Engineering, 2nd Edition, Butterworth-Heinemann, 1991; Daizo Kunii, Octave Levenspiel) proposed undertaking the heat input by means of circulating streams of particles, for example catalyst particles. In this technique, the catalyst particles alternately pass through a production cycle and a regeneration cycle in a circulating fluidized bed. As a result, the particles function not only as a catalyst but also simultaneously as a heat carrier for supply of heat to the endothermic reaction. In the reaction chamber, the catalyst particles are cooled down by the endothermicity of the reaction and are constantly laden with carbon-containing deposits, for example. For heating and for removal of the carbon-containing layer, they are treated with a hot regeneration gas in the heat recovery zone. However, a prerequisite for this technique is particles that are resistant to oxygen and mechanical influences.

US 2002/0007594 discloses a process for parallel preparation of hydrogen and carbonaceous products, in which natural gas is introduced into a reaction space and thermally decomposed in the presence of a carbon-rich solid. US 2002/0007594 discloses that the carbonaceous solid is heated in a reactor separate from the reaction space for the thermal breakdown. The heating is effected by means of the combustion gases that form in a combustion of hydrocarbons or hydrogen. Subsequently, the heated solid is introduced into the reaction space.

The disadvantage of the use of a solid as heat carrier is that the solid has to be heated above the temperature level of the reaction in a separate combustion chamber and circulated between the combustion chamber and the reaction chamber. The handling of the hot solid leads to extreme thermal and mechanical stress on the reactor and the control devices. Moreover, the flow rate of solid-state particles is coupled to the heat demand of the reaction and uniform distribution of the mass flows across the cross section is a necessary condition to achieve optimal heat integration. Consequently, the ratio between the gas stream and the solid stream can be adjusted only within a narrow range. Furthermore, the product stream from the pyrolysis passes through a region of declining temperature in which the reverse reaction can take place.

Thus, in this region of the reactor, the reverse reaction to the target reaction can proceed and reduce the yield of the gaseous target products. For example, the yield loss in the case of methane pyrolysis can be up to 5%, and in the case of the steam reforming of methane up to 50%.

The prior art (e.g. U.S. Pat. No. 6,331,283) also discloses autothermal processes in which the heat required for the endothermic reaction is generated via an exothermic accompanying reaction in the same reaction space. The disadvantage of these autothermal processes is the contamination of the gaseous product stream by the smoke gases, for example, in the case of hydrocarbon pyrolysis, entrainment of C-containing components into the hydrogen-rich product stream. A further disadvantage is the losses in the product yield: in the case of hydrocarbon pyrolysis, substantial loss of the pyrolysis carbon. Moreover, heating of the fuel gas for the exothermic accompanying reaction can be disadvantageous for thermal integration.

U.S. Pat. No. 4,240,805 describes a cyclical stream reforming process for hydrogen production in a fixed bed reactor. In the production phase, the reactant gas is heated up in zone 1 of the reactor, which is filled with solid particles, and converted in zone 2 of the reactor, which is filled with catalyst. The product stream leaves zone 2 at high temperatures and cools down in zone 3, which is filled with inert material. In the regeneration phase, hydrogen and oxygen flow separately through zone 3 in the opposite direction to the product stream and are heated. In zone 2, hydrogen and oxygen are combined, such that the combustion reaction heats zones 2 and 1 and the production phase can begin again.

US 2003/0235529 describes the production of synthesis gas in a cyclically operated 2-zone fixed bed reactor. The first zone of the reactor is filled with catalysts, and the second zone with inert material. In the production phase, the reaction takes place in the first zone and the hot product stream cools down in the second zone. In the regeneration phase, in reverse flow direction, oxygen and fuel flow through the reactor and are combusted at the transition from zone 2 to zone 1 and provide the heat for the next production phase. In FIG. 2 of US2003/0235529, it becomes clear that, in the reforming (reform, 149), the reaction front (right flank) migrates much more quickly than the pure temperature front (left flank). A disadvantage of the mode of operation disclosed in the case of these non-synchronous temperature fronts is that, for establishment of the starting profile for the next cycle, energy is necessarily discharged from the reactor, which results in elevated energy consumption. As illustrated by example 1, there was a deviation by a factor of 4 from the optimal setting of the heat capacity flows between the production phase and the regeneration phase of 1:1 to be able to achieve an acceptable conversion in the reforming. According to example 1, 82.35% of the heat released is utilized for the reforming, and according to example 2 74.64%.

US 2007/0003478 describes the cyclical production of synthesis gas in a 3-zone fixed bed reactor. Zones 1 and 3 are filled with inert material, and zone 2 with catalyst. In the production phase 1, the reactant gas is heated in zone 1. Oxygen is supplied upstream of zone 2, such that sufficient heat is available for the endothermic synthesis gas reaction in zone 2. Subsequently, the product stream cools down in zone 3. In the production phase 2, in reverse flow direction, reactant gas is heated up in zone 3 and oxygen is supplied upstream of zone 2. US 2007/0003478 thus does not describe any regeneration phase. The reaction zone and the mode of operation are symmetrical.

The third concept is based on indirect heat transfer, for example by recuperative means (e.g. EP 15 16 8206) or via heat pipes (e.g. U.S. Pat. No. 4,372,377), from the exothermic to the endothermic reaction chamber. A disadvantage of this concept is the complex internals in the hot section of the reaction chamber that place high material-related and construction demands on the gasket and on the avoidance of thermal stresses. Moreover, these internals disrupt the flow of solids. A further problem with this concept is the fouling of the heat transfer surfaces: for example, in the case of hydrocarbon pyrolysis, the deposition of pyrolytic carbon preferentially on hot surfaces.

The fourth concept is based on the use of gaseous heat carriers for introduction of heat for endothermic breakdown reactions:

WO 2013/004398 discloses that the thermal energy for the heat carriers is generated outside the reaction space and the gaseous heat carriers are inert to the breakdown reaction and/or are a product of this reaction. A disadvantage is that the flow rate of solid particles is coupled to the demands of the thermal integration. Moreover, the product stream from the breakdown reaction passes through a region of declining temperature in which the reverse reaction can take place.

U.S. Pat. No. 2,319,679 discloses a process for the pyrolysis of hydrocarbons to acetylene in a regenerative oven comprising a structured packing of silicon carbide stones. The function of a regenerator is to act as heat storage means for hot offgases from a boiler. This is accomplished in that one of two channels with refractory lining at any time is heated by hot offgases until a switch to the second channel on attainment of a predetermined temperature. The heated channel then heats the fresh gas. At the same time, the other channel is heated again by offgases until there is a switch again. The process is conducted cyclically with a cycle time of 3 to 5 minutes. In the first phase of the cycle, the regenerative oven is heated to temperatures between 1100° C. and about 1600° C. by the offgases from a combustion chamber. In the subsequent production phase, cold process gas is guided through the preheated packing and converted by pyrolysis. Immediately after leaving the regenerator, the pyrolysis gas is introduced into a water bath and quenched in order to suppress further reaction of the acetylene formed. It is a feature of the process that the fittings for control of the process are disposed in a low-temperature region, where they can reliably switch at the required frequency. The disadvantage of this process is the lack of thermal integration in the process gas.

U.S. Pat. No. 2,557,143 discloses a process for the pyrolysis of hydrocarbons to give carbon black and hydrogen in a regenerative oven. The regenerative oven consists of at least two separate apparatuses, a "reactor" and an "oven". The two apparatuses are filled with random packings of thermally stable particles, for example ceramic materials, or of carbon. The process gas from the pyrolysis is solely in contact with the reactor. A second gas stream, e.g. hydrogen or a gas inert to the pyrolysis reaction, circulates as heat carrier between the reactor and the oven. The process is operated cyclically and comprises four phases: a hydrocarbon flows through the preheated packing in the reactor and is converted to hydrogen and thermal black (1); a fuel is combusted and the heat of combustion is stored in the packing of the oven (2); a nonoxidizing gas flows through the preheated packing of the oven (3); the superheated heat carrier stream heats up the packing of the reactor. The pyrolysis generates hydrogen and thermal black. During the startup phase, a steady-state permanent loading of soot builds up in the reactor. Once the state of operation has been established, the carbon black produced is discharged with the process gas.

The disadvantages of this process are: shutoff valves are required in the hot region of the process zone and the product stream from the pyrolysis passes through a region of declining temperature in which the reverse reaction can take place.

U.S. Pat. No. 7,943,808 discloses a cyclical process with periodic reversal of flow for acetylene synthesis in a two-zone reactor. The first and second zones of the reactor are of different configuration. The cross section in the first zone is divided longitudinally into two channels. The cross section of the second zone is homogeneous. During the first half-cycle, a combustion reaction between the first and second zones of the reactor produces heat which is stored in the second zone of the reactor. Subsequently, methane is passed through the reactor in reverse flow direction. At the same time, methane is converted to acetylene in the preheated second reactor zone and quenched rapidly in the first reactor zone. A disadvantage of this process is the complexity of the reactor, caused by the structuring of the cross section in the first reactor zone. This reactor design does not permit supply or removal of solids from the reactor.

It is an object of the present invention to overcome the disadvantages mentioned in the prior art, i.e. to demonstrate a process concept for conducting endothermic gas phase and endothermic gas-solid reactions, in which (i) no valves are required in the hot region of the process zone, (ii) a mode of operation with integrated re-exchange of heat is possible without coupling of the flow rate of solid particles to the requirements of the thermal integration and/or the general heat demand, (iii) a mode of operation is chosen that leads to establishment of a ratio of the heat capacity flows between the production phase and the regeneration phase of close to 1:1 and synchronous temperature fronts are enabled thereby, (iv) any reverse reaction of the gas-solid reaction in the gaseous product stream is ruled out as far as possible, in order to prevent soot formation in the product stream and hence cleaning steps, (v) no handling of hot solids is necessary, and/or (vi) no contamination by autothermal heating, is used. The focus is on objectives (ii) and (iii).

DESCRIPTION OF THE INVENTION

The object is achieved by a process for conducting endothermic gas phase or gas-solid reactions, which comprises conducting the endothermic reaction in a production phase in a first reactor zone, the production zone, which is at least partly filled with solid particles, where the solid particles are in the form of a fixed bed, of a moving bed and in sections/or in the form of a fluidized bed, and drawing off the product-containing gas stream from the production zone in the region of the highest temperature level plus/minus 200 K and guiding the product-containing gas stream through a second reactor zone, the heat recovery zone, which at least partly comprises a fixed bed, where the heat from the product-containing gas stream is stored in the fixed bed, and, in the subsequent purge step, guiding a purge gas through the production zone and the heat recovery zone in the same flow direction, and, in a heating zone disposed between the production zone and the heat recovery zone, introducing the heat required for the endothermic reaction into the product-containing gas stream and into the purge stream or into the purge stream, and then, in a regeneration phase, passing a gas through the two reactor zones in the reverse flow direction and heating up the production zone.

The term "highest temperature level" is understood to mean the highest temperature attained in the respective endothermic reaction. This range in the highest temperature level is preferably plus/minus 150 K, preferably plus/minus 100 K, especially plus/minus 50 K.

The object is achieved more particularly by a process for performing endothermic reactions, comprising process steps (a) introducing a reactant-containing gas into a preheated production zone and conducting the endothermic reaction in the production zone which is at least partly filled with solid particles (process step: production), (b) optionally introducing heat into the product-containing gas stream in a heating zone downstream of the production zone (process step: heat input), (c) transferring heat from the product-containing stream from step (b) to a fixed bed containing especially materials that are inert in respect of the target reaction and are not products of the target reaction in a heat recovery zone downstream of the heating zone (process step: heat storage), (d) purging the production zone and the heat recovery zone with an inert purge gas in flow direction of the reactant-containing gas (process step: purging), (e) introducing heat into the product-containing gas stream in a heating zone downstream of the production zone (process step: heat input), (f) stopping the introduction of reactant-containing gas and introducing a regeneration gas into the heat recovery zone with opposite flow direction compared to the reactant-containing gas, (g) transferring heat from the solid particles and/or structured internals heated in step (c) to the regeneration gas (process step: heat release), (h) transferring heat from the regeneration gas heated in step (g) to the solid particles in the production zone (process step: heating), (i) stopping the introduction of regeneration gas into the heat recovery zone and introducing a reactant-containing gas into a preheated production zone with flow direction analogous to step (a) compared to the regeneration gas.

The object is also achieved by a structured reactor comprising three zones, a production zone containing a packing of solid particles, a heating zone and a heat recovery zone containing a fixed bed, for example packings of solid particles and/or shaped bodies composed of structured regenerator internals, for example monoliths or sheets (see "Regelmäßige Katalysatorformkörper für technische Synthesen" [Regular Shaped Catalyst Bodies for Industrial Syntheses] by Eigenberger et al., VDI, Forschungsberichte [Research Reports], 1993, series 14; No. 112), wherein the packing of solid particles and the fixed bed consist of different materials and solid particles can be introduced and discharged during reactor operation.

The solid packing in the production zone is also referred to hereinafter as "production bed". Advantageously, the production bed is formed from particles in a random arrangement. These particles may be reactive, catalytically active or inert. The fixed bed of the production zone is advantageously a catalyst for an endothermic gas phase reaction, a solid-state catalyst for an endothermic gas-solid reaction, or the product of an endothermic reaction.

The fixed bed in the heat recovery zone is also referred to hereinafter as "regenerator bed". The regenerator bed may advantageously consist of particles in a random arrangement and/or a structured packing of fixed internals. The materials of the regenerator bed may be inert and advantageously not products of the target reaction.

Advantageously, the process of the invention or the reactor of the invention is used in gas-solid reactions.

Advantageously, the process of the invention or the reactor of the invention is used in pyrolysis, steamcracking, dehydrogenation, dehydroaromatization, reforming, the Boudouard reaction, alkane ammodehydrogenation and/or water thermolysis.

$CO_2$ emissions in the process of the invention for 100 kg of hydrogen are advantageously less than 10 kg $CO_2$/kg$H_2$, preferably less than 8 kg $CO_2$/kg$H_2$, especially less than 6 kg $CO_2$/kg$H_2$, especially less than 4 kg $CO_2$/kg$H_2$, especially less than 2 kg $CO_2$/kg$H_2$; the process of the invention is most preferably free of $CO_2$ emissions.

The term "production" is understood to mean the introduction of a reactant-containing gas into the preheated solids packing in the production zone and conversion thereof.

The term "heat input" means the introduction of an oxygen-rich gas into the heating zone and the combustion of a fuel gas present in the main stream from the production zone either during the production step or during the purge step. This fuel gas is preheated by the heat stored in the production bed to temperatures of 350° C. to 1200° C., preferably of 400° C. to 1000° C. Alternatively, the fuel gas can be introduced directly into the heating zone with a sidestream.

The term "storage" is understood to mean the flow through the regenerator bed and the transfer of the tangible heat present in the gas stream to the regenerator bed.

The term "release" is understood to mean the introduction of a regeneration gas into the preheated regenerator bed in the opposite direction to the gas flows during the production phase and the uptake of the tangible heat stored in the regenerator bed.

The term "heating" is understood to mean the flow of the regeneration gases from the regenerator bed through the production bed during the release and the transfer of the tangible heat present in the regeneration gas to the packing of the production bed.

The term "purging" is understood to mean the introduction, in the same direction relative to the gas flows during the production phase, of an inert, for example nitrogen-rich, or exothermically reacting, for example hydrogen-rich, gas into the partly cooled production bed.

The term "holding" is understood to mean the interruption of the flow through the production bed and/or the regenerator bed.

The term "idling" is understood to mean the step in the heating zone during which the product gas or the regeneration gas does not absorb any heat within the heating zone.

The term "expulsion" is understood to mean exchange of the gas contents of the entire reactor. It is thus advantageously possible to avoid contamination of the process gases in the individual steps.

The term "introducing" is understood to mean the introducing of a stream of solids into the production bed at the top. This step can proceed simultaneously with the emptying of part of the production bed out of the lower end of the production zone.

Advantageously, the process of the invention is operated cyclically. Every cycle comprising steps a) to g) is advantageously 2 minutes to 24 hours, preferably 5 minutes to 12 hours, more preferably 10 minutes to 10 hours, especially 30 minutes to 5 hours.

A cycle comprises at least two phases, the production phase comprising steps (a) to (c), i.e. production in the production zone, additional heat input in the heating zone and storage of the heat in the heat recovery zone, and the regeneration phase comprising steps (d) to (g), i.e. release of heat from the heat transfer zone and heating of the production zone.

A cycle may further advantageously comprise the following further steps: holding, purging, drawing off the solid product and/or introducing solid particles. These further steps may be present in every cycle, or else be absent over several cycles. In addition, the step of drawing-off may extend over several cycles, and optionally be effected continuously. The frequency of drawing-off the solid product can be designed with reference to process-specific criteria. The following table lists criteria for different processes:

| Process | Criterion for emptying/replacement of solid particles in the production zone |
| --- | --- |
| Pyrolysis | Increase in mass of the carrier |
| Dehydrogenation | Accumulation of coke<br>Irreversible deactivation<br>Abrasion |
| Dehydroaromatization | Accumulation of coke<br>Irreversible deactivation<br>Abrasion |
| Steamcracking | Accumulation of coke<br>Irreversible deactivation |
| Reverse Boudouard reaction | Decrease in mass of the solid coke reactant |
| Deacon | Decrease in mass by "leaching" of the active solids |
| Water thermolysis | Irreversible deactivation<br>Abrasion |
| $NH_3$ cleavage | Irreversible deactivation |

It is advantageously possible for two or more steps to run synchronously in time. For example, the steps of drawing-off and introduction of solid particles can run synchronously. In addition, the steps of purging, drawing-off and/or introduction of solid particles can run synchronously.

Continuous introduction and/or continuous drawing-off of solid particles is also possible. In this case, the steps of "drawing-off" and/or "introducing" proceed synchronously with all other steps.

The relative duration of the individual process steps that proceed in the production zone, based on the duration of an entire period, is within the following ranges:

The production phase advantageously takes between 10% and 80%, preferably between 20% and 60% of the period duration. The purge step in the production phase advantageously takes between 0% and 50%, preferably between 10% and 40%, especially between 30% and 40%, of the period duration. The regeneration phase advantageously takes between 10% and 80%, preferably between 20% and 60% of the period duration; if there is a purge step, the regeneration phase advantageously takes 30% to 40% of the period duration.

The duration of the steps in the heating zone and in the heat recovery zone is advantageously synchronized with the duration of the steps in the production zone. If no purge step is envisaged in the cycle, the heat input in the heating zone takes place during the production step (see FIG. 3). Otherwise, advantageously, alternatively or additionally, the heat input in the heating zone takes place simultaneously with the purge step in the production zone (see FIG. 4 and FIG. 5), preferably alternatively. The storage step in the heat recovery zone advantageously takes exactly as long as the production step and the purge step together.

The relative duration of the individual process steps advantageously depends on how many reactors of the invention are combined to form a plant. With the aim of quasi-continuous production, the following rule is established:

| Number of reactors per plant | Minimum proportion of the production step per cycle |
| --- | --- |
| 2 | 50% |
| 3 | 33% |
| 4 | 25% |

The intended state of operation is advantageously the cyclically steady or periodic state. This state is established in asymptotic manner in unperturbed operation and is characterized in that the states of operation of the reactor are the same in time intervals corresponding to the cycle period.

The Production Phase:

The production phase of the invention comprises at least three steps in flow direction of the reactant gas: (a) "production", (b) "heat input", and (c) "storage" in the heat recovery zone.

Production Step:

In production step (a), the reactant-containing stream is advantageously guided through a preheated packing of thermally stable solid particles in the production zone and converted.

The reactant-containing stream is advantageously a hydrocarbon-containing gas or vapor, i.e. a gaseous phase of a substance in equilibrium with the liquid phase. Preference is given to natural gas H, natural gas L, refinery fractions such as liquefied gases (propane, butane), or naphtha, coproduct gases and biogases as described, for example, in WO 2014/095661, or mixtures thereof. A preferred mixture comprises natural gas and liquefied gas.

Alternatively, the reactant-containing stream is a carbon monoxide-containing, water-containing, hydrogen-containing, HCl-containing and/or (bio)ethanol-containing gas or vapor. These reactants may optionally be used in a mixture of hydrocarbons.

The following reactions are summarized in tabular form by way of example:

| Process | Crude gas (reactant) | Product | Typical catalyst/solid-state catalyst |
|---|---|---|---|
| Pyrolysis | natural gas, liquefied gas, naphtha, ethanol | carbon hydrogen | coke |
| Steamcracking | liquefied gas, naphtha, steam | olefins (ethylene, propylene, . . .) | coke |
| Dehydrogenation | propane, steam | propylene | $Cr_2O_3$, Pt—Sn |
|  | raffinate II, steam | butenes |  |
|  | ethylbenzene, steam | styrene | $Fe_2O_3/K_2CO_3$ |
| Dehydroaromatization | natural gas, liquefied gas | benzene | Mo/zeolite |
| Reforming | natural gas (with steam/$CO_2$) | synthesis gas $CO:H_2$ | Ni, hexaaluminates, Ru |
| Boudouard reaction | $CO_2$ | CO | coke |
| Alkane ammodehydrogenation | naphtha, ammonia, natural gas, liquefied gas | HCN | coke |
| Water thermolysis | steam | H2/O2 | ferrites |
| Al(OH)$_3$ calcination | air | $Al_2O_3$ | Al(OH)$_3$, bauxite |
| Lime burning | air, $CO_2$ | CaO, $CO_2$ | lime |

With particular preference, the process of the invention is used in the preparation of hydrogen, of synthesis gas, of styrene, propene, butene and/or benzene, of acetylene, of carbon monoxide, of hydrogen cyanide, and in the calcination of aluminum hydroxide. Preference is given to the following processes: steam reforming and dry reforming, the thermolysis of water, the dehydrogenation of ethylbenzene to styrene, of propane to propene, of butane to butene and/or of cyclohexane to benzene, the pyrolysis of hydrocarbons, especially the pyrolysis of methane, ethane, propane and/or butane, and pyrolytic acetylene production, the dehydroaromatization of methane to propane, the ammodehydrogenation of methane to propane, the Boudouard reaction, calcination (breakdown of hydroxides and carbonates).

The feed temperature of the reactant-containing stream is advantageously from −150° C. to 750° C., preferably from −75° C. to 600° C., more preferably from 4° C. to 400° C., especially from 20° C. to 250° C. The advantage of the low temperatures is that the gas from a cryogenic purification stage can be used directly and/or the product gas can be fed directly into a cryogenic purification stage, with only a small lowering of temperature required for fractionation. Advantages of the higher temperatures are that high boilers cannot condense out and the reactor volume can be utilized completely for the reaction.

The preheating temperature is the target value to which the production bed is advantageously heated in the cyclically steady state prior to each production step. Advantageously, a predominant portion of the production bed is heated to this preheating temperature, advantageously between 30% and 100% of the bed, preferably between 40% and 100%, more preferably between 50% and 100%, especially between 60% and 100% of the bed.

For the preferred variants of the process of the invention, the value ranges for the preheating temperatures are summarized in tabular form:

| | Preheating temperature | | | |
|---|---|---|---|---|
| | min [° C.] | | max [° C.] | |
| Reaction | Lower limit | Preferred lower limit | Preferred upper limit | Upper limit |
| Pyrolysis (natural gas, liquefied gas, naphtha) | 900 | 1300 | 1800 | 2000 |
| Steamcracking | 900 | 1000 | 1500 | 2000 |
| Dehydrogenation of propane | 550 | 600 | 700 | 750 |
| Dehydrogenation of raffinate II | 500 | 550 | 650 | 700 |
| Dehydrogenation of ethylbenzene | 550 | 600 | 700 | 750 |
| Dehydroaromatization (natural gas) | 600 | 700 | 800 | 900 |
| Reforming of natural gas (steam/CO2) | 600 | 900 | 1500 | 1800 |
| Boudouard reaction | 700 | 800 | 1500 | 1800 |
| Alkane ammodehydrogenation | 1200 | 1400 | 1700 | 2000 |
| Al(OH)$_3$ calcination | 1000 | 1200 | 1200 | 1700 |
| CaCO$_3$ calcination | 700 | 900 | 900 | 1500 |

In the pyrolysis of hydrocarbons, the production bed is advantageously preheated to 900 to 2000° C., preferably to 1100 to 1900° C., more preferably to 1300 to 1800° C. and especially to 1400 to 1700° C. (preheating temperature).

The difference between the feed temperature of the reactant-containing stream and the temperature of the preheated solid packing in the reaction region is advantageously 500 to 2000 K, preferably 700 to 1900 K, more preferably 900 to 1800 K, especially 1000 to 1700 K.

The onset temperature is the temperature above which the endothermic reaction proceeds at reaction rates of industrial relevance. For the preferred variants of the process of the invention, the value ranges for the onset temperatures are summarized in tabular form:

| Reaction | Onset temperature | | | |
|---|---|---|---|---|
| | min [° C.] | | max [° C.] | |
| | Lower limit | Preferred lower limit | Preferred upper limit | Upper limit |
| Pyrolysis (natural gas, liquefied gas, naphtha) | 500 | 700 | 1000 | 1200 |
| Steamcracking | 500 | 600 | 800 | 1000 |
| Dehydrogenation of propane | 350 | 400 | 450 | 500 |
| Dehydrogenation of raffinate II | 350 | 400 | 450 | 500 |
| Dehydrogenation of ethylbenzene | 400 | 450 | 500 | 550 |
| Dehydroaromatization (natural gas) | 400 | 500 | 600 | 700 |
| Reforming of natural gas (steam/CO2) | 350 | 400 | 500 | 600 |
| Boudouard reaction | 400 | 500 | 700 | 800 |
| Alkane ammodehydrogenation | 400 | 600 | 800 | 1000 |
| Al(OH)$_3$ calcination | | 400 | 700 | |
| CaCO$_3$ calcination | | 550 | 700 | |

The reactant-containing stream advantageously has a flow rate in the production zone of 0.001 to 20 m/s, preferably of 0.01 to 10 m/s, further preferably of 0.05 to 5 m/s, especially of 0.1 to 2 m/s. The term "flow rate" means the superficial velocity under standard conditions. This is defined as the loading of matter in the reaction zone irrespective of variation in the operating parameters (pressure, temperature).

Advantageously, the product-containing stream on exit from the production zone has an absolute pressure of 0.1 to 100 bar, preferably of 0.3 to 80 bar, further preferably of 1 to 60 bar, especially of 3 to 40 bar.

Advantageously, the average residence time of the reactant-containing gas stream in the region of the production zone which is at the preheating temperature is 0.1 to 900 s, preferably 0.2 to 300 s, further preferably 0.5 to 60 s, especially 1 to 30 s. In analogy to the flow rate, what is meant by the residence time in the production bed is the quotient of the superficial volume of the production zone and the volume flow rate of the reactant-containing gas stream under standard conditions.

For example, the space-time yield of hydrogen production in the case of natural gas pyrolysis is 10 to 10 000 kg H$_2$/h/m$^3$, preferably 100 to 1000 kg H$_2$/h/m$^3$.

The production bed is advantageously a bulk material bed, i.e. a random packing of solid particles. Alternatively, it is also possible to provide fixed internals in the production zone, for example in the form of heating elements or in the form of a fixed, regular packing. The production bed in this case consists of a mobile part and a fixed part.

The solid particles of the production bed are advantageously thermally stable within the range from 1000 to 2800° C., preferably 1300 to 2800° C., more preferably 1500 to 2800° C., especially 1600 to 2800° C.

Examples of useful thermally stable solids advantageously include ceramic carrier particles, especially materials according to DIN EN 60 672-3, for example alkali metal aluminosilicates, magnesium silicates, titanates, alkaline earth metal aluminosilicates, aluminum silicates and magnesium silicates, mullite, alumina, magnesia and zirconia. In addition, non-standardized ceramic high-performance materials, for example quartz glass, silicon carbide, boron carbide and/or nitrides, may serve as thermally stable solids.

Also advantageous is the use of carbon-containing material in pellet form. In the present invention, a carbon-containing pellet material is understood to mean a material that advantageously consists of solid grains having at least 50% by weight, preferably at least 80% by weight, further preferably at least 90% by weight of carbon, further preferably at least 95% by weight, especially at least 98% by weight, of carbon. The carbon-containing pellet material advantageously has a grain size, i.e. an equivalent diameter determinable by sieving with a particular mesh size, of 0.05 to 100 mm, preferably 0.1 to 10 mm, further preferably 0.2 to 5 mm, especially 0.3 to 3 mm.

Advantageously, the density of the carbon-containing material is 0.15 to 2.25 g/mL, preferably 0.3 to 2 g/mL, further preferably 0.65 to 1.85 g/mL, especially 0.9 to 1.7 g/mL.

Advantageously, the porosity of the carbon-containing material is 0 to 0.95 mL/mL, preferably 0.1 to 0.85 mL/mL, further preferably 0.15 to 0.7 mL/mL, especially 0.25 to 0.6 mL/mL.

Advantageously, the carbon-containing material has macroporosity. The average pore radius is advantageously 0.01 to 50 μm, preferably 0.1 to 20 μm, especially 0.5 to 5 μm. The specific surface area is advantageously 0.02 to 100 m$^2$/g, preferably 0.05 to 10 m$^2$/g, especially 0.2 to 2 m$^2$/g.

The carbon-containing pellet material is advantageously spherical. In the process of the invention, it is possible to use a multitude of different carbon-containing pellet materials. A carbon-containing pellet material of this kind may consist, for example, predominantly of charcoal, coke, coke breeze and/or mixtures thereof. In addition, the carbon-containing pellet material may comprise 0% to 15% by weight based on the total mass of the pellet material, preferably 0 to 5% by weight, of metal, metal oxide and/or ceramic.

In the present invention, "coke" is understood to mean a porous fuel having a high carbon content (proportion by mass of C>85%).

The ceramic carrier particles advantageously have a non-porous and smooth surface, defined by the roughness, or by the nature of the surface treatment, for example

| Processing | Average roughness Ra [μm] | Roughness depth Rz [μm] |
|---|---|---|
| sintered only, "as fired" | 0.7 | 4.8 |
| scoured | 0.35 | 3.6 |
| ground | 0.3 | 3.7 |
| polished* | 0.1 | 2.1 |

*Brevier Technische Keramik 10.5.4.4

It is advantageous in the case of the ceramic supports when the pyrolytic carbon can be detached easily from the surface. Advantageous polished carrier particles are those made of corundum, stoneware or quartz glass.

Advantageously, the falling speed of the stream of solids in the production zone, averaged over a period, is in the range from 0 m/h to 50 m/h, preferably 0 m/h to 10 m/h, especially 0 m/h to 5 m/h. More particularly, the flow rate of solids may correspond to the production rate plus/minus 10% of the solid product, such that the holdup in the production zone remains constant.

Advantageously, the loading and unloading in the production zone with solid particles takes place while no reactant-containing gas, preferably no reacting gas, is flowing through the production zone, especially while no gas is flowing through the production zone.

The solid packing in the production zone may have different states of fluidization during the production step: advantageously a fixed bed, a moving bed or a fluidized bed. The fluidization state may be homogeneous or inhomogeneous over the height of the production zone. More particularly, the production zone may be divided vertically into zones with different fluidization states: for example a fixed bed or moving bed in the lower section of the production zone and a fluidized bed or moving bed in the upper section of the product exit.

The intimate contact between the gaseous reaction mixture and the solids in the production zone and in the heat recovery zone results from the specific interfacial area between the solid packing and the gas phase, which is greater than 50 m$^2$/m$^3$, preferably greater than 100 m$^2$/m$^3$, more preferably greater than 500 m$^2$/m$^3$. It results in intense heat exchange with a coefficient of heat transfer of advantageously greater than 10 W/m$^2$/K, preferably greater than 50 W/m$^2$/K, more preferably greater than 100 W/m$^2$/K between the gaseous reaction mixture and the solids.

Preferably, the process of the invention for pyrolysis of hydrocarbons is conducted without using an active metal-containing catalyst.

Alternatively, the solid particles of the production bed may also include catalysts, or the bed of solids may consist exclusively of catalysts, and so the production bed is advantageously a catalyst bed. Advantageous catalysts are known to those skilled in the art for the abovementioned reactions, for example zeolite-containing catalysts for dehydroaromatization, Ni-containing catalysts for reforming, Pt-, Fe- or Cr-containing catalysts for dehydrogenation.

Alternatively, the fixed bed may comprise a solid, reactive component which is converted reversibly in a forward reaction and a reverse reaction within one cycle. For example, in this way, ferrites can be used for thermolysis of water (Solar Energy, 81(5), 623-628, 2007). In addition, it is possible, for example, to calcine Al(OH)$_3$ to Al$_2$O$_3$ or CaCO$_3$ to CaO.

In the pyrolysis of hydrocarbons, the target products of this reaction are hydrogen and carbon. The hydrogen advantageously flows through the packing of solid particles, while the carbon is largely deposited on the solid particles. The degree of deposition of the carbon on the solid particles is advantageously in the range from 85% to 100%, preferably 90% to 100%, more preferably 95% to 100%, especially 99% to 100%.

Purging Step:

For the purging step, the gas composition in the feed to the production zone is advantageously switched from the reactant-containing stream of the production step to a purge gas. The purge gas may have different compositions. For example, the purge gas comprises hydrogen, carbon monoxide, carbon dioxide, steam, nitrogen, argon or a mixture of these gases. The gas stream used during the purge step may be imported or may be a recycle stream from the process.

Advantageously, the heat input in the heating zone takes place simultaneously with the purge step in the production zone (see FIG. 4 and FIG. 5). Otherwise, if no purge step is envisaged in the cycle, the heat input advantageously takes place in the heating zone during the production step (FIG. 3 and FIG. 6). The storage step in the heat recovery zone advantageously takes just as long as the production step and the purge step together.

The feed temperature of the gas stream into the production bed during the purge step is advantageously −150 to 750° C., preferably −75 to 600° C., more preferably 4 to 400° C., especially 20 to 250° C. This is analogous to the feed temperature for the reactant-containing gas and the regeneration gas.

During the purge step, the gas stream advantageously has a flow rate in the production zone of 0.001 to 20 m/s, preferably of 0.01 to 10 m/s, further preferably of 0.05 to 5 m/s, especially of 0.1 to 2 m/s.

The ratio between the heat capacity of the gas supplied to the reactor during the purge step and the heat capacity of the reactant-containing gas in the feed to the production zone during the production step is between 0% and 400%, preferably between 0% and 200%.

As a guide value, the heat capacity of the gas stream in the respective step is ascertained by the following relationship:

$$C_i = \dot{M}_i^+ \cdot c_p(\overline{T}) \cdot \Delta t_i \text{ where:}$$

$$C_i \left[\frac{J}{kg}\right]:$$

heat capacity of the gas in step i $$\dot{M}_i^+ \left[\frac{kg}{s}\right]:$$

average feed mass flow rate in step i $$c_p(\overline{T}) \left[\frac{J}{kg \cdot K}\right]:$$

specific heat capacity of the gas with the feed composition at an average temperature between the feed temperature and the preheating temperature.

$\Delta t_i$ [s]: duration of step i

The serial variable i may take the following meaning: "production", "purging", "storing", "releasing".

The relative duration of the purge step, based on the duration of a full period, is advantageously between 0% and 50%, preferably between 10% and 40%.

Using an inert purge gas, the heating zone is advantageously supplied in a controlled manner with a fuel gas and an oxidizing agent, such that the heat of combustion raises the mixture temperature at the outlet of the heating zone to the desired preheating temperature.

When hydrogen is used as fuel, the water generated can advantageously be condensed out and the nitrogen can be recycled as cycle gas.

The solid packing in the production zone may have different states of fluidization during the purge step analogously to the production step: advantageously a fixed bed, a moving bed or a fluidized bed, especially a fixed bed.

Heat Input Step:

In step (b), heat is supplied to the product-containing gas stream, especially hydrogen-containing gas stream, leaving the production zone, and this increases the thermal energy of the gas stream. An increase in the thermal energy can be achieved by raising the gas temperature to the level of the required preheating temperature and/or by increasing the gas rate to the level of the required preheating temperature. The first effect is advantageously achieved by partial combustion of the combustible constituents of the product gas in the heating zone. The second effect is achieved by the introduction of the flue gases from an external combustion chamber as gaseous heat carrier into the heating zone (hot gas feeding). Advantageously, the increase in the thermal energy is achieved by raising the gas temperature to the level of the required preheating temperature.

Advantageously, the steps of "production" and "heating" run synchronously. Preferably, the steps of "purging" and "heating" run synchronously.

The heating zone may be a mixing chamber. The walls of the heating zone may be lined with a thermally stable, chemically stable, inert and thermally insulating layer. The heating zone may comprise separate feed conduits for sidestreams such as fuel gas/oxidizing agent-containing gas and/or a gaseous heat carrier. The heating zone may comprise guide plates/internals to direct streams (static mixers) and/or for feeding and distribution of sidestreams. The heating zone may also comprise a device for ignition of a combustible mixture.

The temperature of the gas stream that leaves the heating zone is controlled to the predetermined value for the preheating temperature.

The heat input can be effected by any methods known to those skilled in the art:

For example, in the heating zone, the gas stream comprising combustible components that leaves the production zone is mixed with an oxidizing agent-containing, e.g. oxygen-containing, gas stream which is fed into the heating zone via separate conduits, and partially combusted. The product-containing gas stream is preheated here by the heat stored in the production bed to temperatures of 350° C. to 1200° C., preferably of 400° C. to 1000° C.

For example, a heat input can be effected in that an inexpensive fuel gas, e.g. natural gas, an inexpensive liquid fuel, e.g. naphtha, and/or an inexpensive solid fuel, e.g. pulverized coal, is advantageously combusted in an external combustion chamber and the hot flue gas is introduced into the heating zone via separate conduits. Alternatively, the fuel and the oxidizing agent can be introduced into the heating zone via separate conduits and combusted therein.

For example, a heat input can be effected by blowing in pulverized coal which is converted primarily to CO at high temperatures of advantageously 1200 to 2200° C., preferably 1400 to 2100° C., more preferably 1500 to 2000° C., especially 1600 to 1900° C., and with a stoichiometric excess. In this case, the product gas may comprise significant amounts of COx. For particular applications, this proportion can be processed specifically as synthesis gas.

Moreover, the heat input can be effected by feeding in a superheated inert gas, for example nitrogen. The superheated inert gas may, for example, be heated up beforehand in a plasma burner, or such a plasma burner may be integrated into the heating zone.

Alternatively, a heat input can be effected by indirect heating. The product-containing gas stream and the fuel gas, for example an air/natural gas mixture, may advantageously be guided through adjacent channels. The heat of combustion is transferred through the channel wall to the process gas. This variant has the advantage that the product gas can be obtained in undiluted form.

A specific form of indirect heating is electrical resistance heating. According to the invention, the electrical heating elements are in thermal contact with the gas stream. Advantageously, the resistance elements are embedded in a pile of thermally stable particles through which the product gas flows.

Alternatively, the electrical heating elements may advantageously be embedded in a wall which is in thermal contact with the gas stream.

Preferably, the heat for the endothermic reaction, however, is introduced using the direct introduction of energy into the product-containing gas stream or into a purge stream.

For example, the product gas stream that enters the heating zone is superheated by a temperature differential of 0 K to 2000 K, preferably of 0 K to 1000 K.

The oxygen-containing gas is, for example, air or enriched air, where the oxygen content of the oxygen-containing gas is advantageously between 20% and 100%, preferably between 40% and 100%, more preferably between 50% and 100%, especially between 60% and 100%. Very particular preference is given to oxygen of technical-grade purity (advantageously greater than 95% by volume of oxygen, preferably greater than 99% oxygen, more preferably greater than 99.5% oxygen).

It should advantageously be ensured that no ignitable mixture arises in the inlets of the side feed to the heating zone. This is ensured, for example, in that the inlets of the side feed that guide the oxidizing agent-containing gas stream to the heating zone, before commencement of the heat input step and at the end of the heat input step, are purged in a defined manner with pure nitrogen, argon, $CO_2$, $H_2O$ vapor or mixtures of these gases. The gas volume conveyed through the conduits during these intermittent inertization steps corresponds to five times to fifty times the volume of the conduit. Alternatively, it is possible to permanently feed nitrogen, argon, $CO_2$, $H_2O$ vapor or mixtures of these gases into the inlets of the side feed.

The entry temperature of the oxidizing agent-containing gas stream is advantageously between room temperature and 1500° C., preferably between 150 and 1100° C., more preferably between 300 and 900° C., especially between 400 and 650° C.

During the heat input step, the volume flow ratio of oxygen stream to product-containing gas stream is advantageously between 0.004 and 0.16, preferably between 0.008 and 0.12, more preferably between 0.012 and 0.08, especially between 0.016 and 0.04.

As an alternative to oxygen, it is also possible to use other oxidizing agents, for example NO or $N_2O$.

The mixing temperature of the gas stream at the exit from the heating zone corresponds to the required preheating temperature. The difference from the target value is between −200 and +200K, preferably between −100 and +100K, more preferably between −50K and +50K.

The ratio between the heat capacity of the gas fed in via the side feed and the heat capacity of the reactant-containing gas in the feed to the production zone is between 0 and 5, preferably between 0 and 1, more preferably between 0 and 0.5, most preferably between 0 and 0.1.

As a guide value, the heat capacity of the gas stream in the respective zone is advantageously ascertained by the following relationship:

$$C_i = \dot{M}_i^+ \cdot c_p(\overline{T}) \cdot \Delta t_i \text{ where:}$$

$C_i \left[\dfrac{J}{kg}\right]$:

heat capacity of the gas in zone i $\dot{M}_i^+ \left[\dfrac{kg}{s}\right]$:

average feed mass flow rate in zone i $c_p(\overline{T}) \left[\dfrac{J}{kg \cdot K}\right]$:

specific heat capacity of the gas with the feed composition at an average temperature between the feed temperature and the preheating temperature.

$\Delta t_i$ [s]: duration of step i

The serial variable i may take the following meaning: "production zone", "heat recovery zone".

During the heat input step, the heat output based on the volume of the heating zone is 0.1 MW/m³ to 50 MW/m³, preferably from 0.5 MW/m³ to 20 MW/m³, especially from 1 MW/m³ to 10 MW/m³.

For example, the heat input is distributed between one or more heating zones installed along the heat recovery zone. This variant is shown in FIG. 6. The number of side feeds is advantageously ascertained by the following rule:

$$n_{inj} = 1 + \text{int}\left(\dfrac{X_{eq}}{\Delta T_{eff}} \cdot |\Delta T_{ad}|\right)$$

where $n_{inj}$: number of side feeds
int: function: integer part of a real number
$X_{eq}$ [%]: equilibrium conversion of the reactant achievable at the required preheating temperature during the production phase.

$\Delta T_{eff}$ [K]: effective rise in temperature within the reaction zone. $\Delta T_{eff}$ corresponds to the difference between the required preheating temperature and the onset temperature of the endothermic reaction.

$|\Delta T_{ad}|$[K]: absolute magnitude of the adiabatic change in temperature of the endothermic reaction (for definition see http://elib.uni-stuttgart.de/bitstream/11682/2350/1/docu_FU.pdf page 31).

For the determination of the position of the feeds, a length scale is crucial, which can be referred to in an illustrative manner as "movement interval of a thermal front". The movement interval of a thermal front is determined by the following rule:

$$L_{th} = \dfrac{(\dot{m} \cdot c_p)_g}{(\rho \cdot c)_{fxb}} \cdot \Delta t$$

where
$L_{th}$[m]: movement interval of a thermal front.

$\dot{m}_g \left[\dfrac{kg}{m^2 \cdot s}\right]$:

superficial velocity of the gas flow in the heat recovery zone.

$c_{p,g} \left[\dfrac{J}{kg \cdot K}\right]$:

specific heat capacity of the gas on entry into the heat recovery zone.

$\rho_{fxb} \left[\dfrac{kg}{m^3}\right]$:

density of the solid packing in the heat recovery zone.

$c_{fxb} \left[\dfrac{J}{kg \cdot K}\right]$:

specific heat capacity of the solid packing in the heat recovery zone.
$\Delta t$ [s]: duration of the relevant time interval (in general, duration of the storage step within the cycle).

The positions of the side feeds are advantageously fixed by the following rules: (i) the distance of the first side feed from the start of the regenerator bed in flow direction during the production phase advantageously corresponds to the movement interval of the thermal front during the production phase. (ii) the distance between successive side feeds advantageously corresponds to the movement interval of the thermal front during the production phase.

This variant is more preferred when no purge step is envisaged in the cycle. Compared to the arrangement of the heating zone between the production zone and the heat recovery zone, a smaller sidestream flow is required in order to introduce the heat for the storage step.

"Storage" Step

In step (c), the product-containing gas stream is guided through a fixed bed in the heat recovery zone, for example a packing of solid particles and/or structured regenerator internals. This advantageously cools the gas stream and the heat is stored in the solid packing.

Advantageously, some of the regenerator bed is heated to the required preheating temperature for the production step, advantageously from 10% to 100% of the bed, preferably from 30% to 100%, more preferably from 40% to 100%, especially from 50% to 100% of the bed.

The heat transfer resistance on heat exchange between the gas and the fixed bed in the regenerator bed advantageously has a length of the transfer units or height-of-transfer units (HTU) of 0.01 to 5 m, preferably 0.02 to 3 m, more preferably from 0.05 to 2 m, especially from 0.1 to 1 m. The definition of HTU is adopted from http://elib.uni-stuttgart.de/bitstream/11682/2350/1/docu_FU.pdf page 74.

The exit temperature of the product-containing stream from the regenerator bed varies with the time within the storage step. Typically, in the first half of the storage step, the rise in the exit temperature is less than 20%, preferably less than 10%, further preferably less than 5%, based on the difference between the preheating temperature and the starting temperature at the exit of the heat transfer zone at the start of the storage step.

In the second half of the storage step, the exit temperature rises continuously. The difference between the exit temperature at the end and at the start of the storage step is between 1% and 100%, preferably between 10% and 70%, further preferably between 20% and 50%, of the difference between the preheating temperature and the starting temperature at the exit of the heat transfer zone at the start of the storage step.

Advantageous solid particles for the regenerator bed are packings of materials that are chemically inert in relation to the reverse reaction of the respective endothermic reaction, e.g. ceramic material. Advantageous ceramic materials are: ceramic materials according to DIN EN 60 672-3, especially alkali metal aluminosilicates, magnesium silicates, titanates, alkaline earth metal aluminosilicates, aluminum silicates and magnesium silicates, mullite, alumina, magnesia and/or zirconia, and non-standardized ceramic high-performance materials, especially quartz glass, silicon carbide, boron carbide.

Advantageous packing forms for the regenerator bed are (i) random packing of shaped bodies, e.g. spheres, cylinders, rings, saddles etc., (ii) structured packing of monoliths, e.g. honeycombs, refractory rocks, (iii) structured packing of profiled plate assemblies ("Hasche tiles"; see U.S. Pat. No. 2,815,198).

In step (c), the yield losses of the gaseous product of gas-solid reactions, for example of the hydrogen from the pyrolysis of hydrocarbons, are advantageously less than 10%, less than 5%, especially less than 0.5%. This advantageous property results from the separation between the gaseous reaction product and the solid reaction product at the highest temperature level in the production zone. Thus, during the cooling in a chemically inert ceramic packing, the co-reactant is absent for the reverse reaction.

Advantageously, the storage step proceeds synchronously in time with the steps of "production" and/or "purging" in the production zone and with the "heat input" step in the heating zone. If no purge step is envisaged in the cycle, the heat input in the heating zone advantageously takes place during the production step (FIG. 3 and FIG. 6). Otherwise, the heat input advantageously takes place in the heating zone simultaneously with the purge step in the production zone (see FIG. 4 and FIG. 5). The storage step in the heat recovery zone advantageously takes exactly as long as the production step and the purge step together.

The ratio between the heat capacity of the gas guided through the regenerator bed during the storage step and the sum total of the heat capacities of the gases that are introduced into the production bed and into the heating zone during the production step and optionally during the purge step is between 0.5 and 2, preferably between 0.8 and 1.2.

The Regeneration Phase:

In the regeneration phase, advantageously, the feed is switched from reactant-containing gas into the production zone to a regeneration gas into the heat recovery zone. The regeneration gas is advantageously passed through the reactor in the opposite direction to the reactant-containing and product-containing stream, especially hydrocarbon stream.

This regeneration gas is, for example, an inert gas and/or a gaseous product of the reaction from step a) and/or a gas mixture from the further process chain/process environment (see example), for example—in the case of methane pyrolysis—the purge gas from the pressure swing adsorption for hydrogen purification. The regeneration gas used is preferably nitrogen, hydrogen, carbon monoxide, carbon dioxide, steam and/or argon or a mixture of these components.

Essentially two steps proceed during the regeneration phase: (i) the release of heat in the regenerator bed and (ii) the heating of the production bed.

Release:

The regeneration gas advantageously absorbs heat in the heat recovery zone. The regeneration gas advantageously has a feed temperature into the heat recovery zone advantageously of −150° C. to 750° C., preferably of −75° C. to 600° C., more preferably of 4° C. to 400° C., especially of 20° C. to 250° C. The feed temperature is as close as possible to the ambient temperature, i.e. within the temperature range between −20° C. and 150° C. This is analogous to the feed temperature for the reactant-containing gas.

The gas stream of the regeneration gas advantageously has a flow rate of 0.001 to 20 m/s, preferably of 0.01 to 10 m/s, further preferably of 0.05 to 5 m/s, especially of 0.1 to 2 m/s.

The regeneration gas advantageously has an exit temperature from the heat recovery zone of 900 to 2000° C., preferably of 1100 to 1900° C., more preferably of 1300 to 1800° C., especially of 1400 to 1700° C.

The regeneration gas is guided from the heat recovery zone via the heating zone into the production zone. In the regeneration phase, a possible heat input in the heating zone with a heat output based on the volume of the heating zone is advantageously less than 100 kW/m$^3$. Preferably, the heating zone is idling, i.e. in active, during the regeneration phase; there is advantageously no heat input.

Alternatively, during the regeneration phase, an oxidizing agent-containing gas and a fuel gas, e.g. natural gas or an energy-rich purge gas, can optionally be introduced into the heating zone. The combustion can advantageously raise the temperature of the regeneration gas by 0 to 800 K, preferably 0 to 500 K, more preferably 0 to 300 K, especially 0 to 100 K.

The ratio between the heat capacity of the gas fed into the regenerator bed during the heat release and the gas fed into the regenerator bed during the heat storage is between 0.5 and 2, preferably between 0.8 and 1.2.

Heating:

During the regeneration phase, heat exchange advantageously takes place in the production zone between the regeneration gas and the solid particles in the production bed. This advantageously cools down the gas stream of regeneration gas and stores the heat in the solid particles. In this way, the subsequent production phase is advantageously supplied, i.e. the production bed is adjusted to the required preheating temperature. The regeneration gas can advantageously be circulated.

The exit temperature of the regeneration gas from the production bed varies with time within the phase. Typically, in the first half of the heating step, the rise in the exit temperature is less than 20%, preferably less than 10%, further preferably less than 5%, based on the differential between the preheating temperature and the starting temperature at the exit from the production zone at the start of the heating step.

In the second half of the heating step, the exit temperature rises continuously. The differential between the exit temperature at the end and at the start of the heating step is between 1% and 100%, preferably between 10% and 70%, further preferably between 20% and 50%, of the differential between the preheating temperature and the starting temperature at the exit from the production zone at the start of the heating step.

If the production bed includes a catalyst bed, it is advantageously possible in the regeneration phase to free the catalyst bed of deposits that cause reversible deactivation, for example. This can be achieved by heating and optionally by establishment of a suitable atmosphere, for example steam content, in order to gasify coke deposits, or, for example, oxygen in order to burn coke deposits.

Advantageously, the heating step in the production bed and the "heat release" step in the heat recovery zone run synchronously, meaning that both steps are started at the same time and last for exactly as long.

The ratio between the heat capacity of the gas supplied via the production bed during the heating and the gas supplied to the regenerator bed during the heat release is between 0.5 and 2, preferably between 0.8 and 1.2.

Further Steps:

Optionally, further steps can be integrated into the cycle, for example: (i) introducing fresh solid particles into the production bed and/or emptying the solid product out of the production bed, (ii) expulsion, wherein the gas contents of the reactor are exchanged in order to avoid contamination of the process gases in the individual steps.

Step: Introducing/Emptying Solids

With regard to the solid particles in the production bed, the process can advantageously be executed (quasi-)continuously or batchwise.

In quasi-continuous mode, within each cycle, some of the solids (solid product, spent solid-state catalyst, deactivated catalyst) are advantageously drawn off from the production bed and fresh solids (carrier, solid-state catalyst or catalyst) are introduced into the production bed, such that, in the cyclically steady operating state, the amount of solids, the composition and the particle size distribution in the production bed at the start of two successive cycles are advantageously identical.

The filling and emptying of solids can advantageously be conducted either continuously or in cycles.

In batchwise mode, an initial charge of solids is advantageously neither replenished nor drawn off over multiple cycles. Advantageously, the batch time is between one cycle and 100 000 cycles, preferably between one cycle and 1000 cycles, more preferably between one cycle and 100 cycles. After the batch time has elapsed, the solids (solid product, spent solid-state catalyst, deactivated catalyst) can be fully or partly emptied and fresh solids (carrier, solid-state catalyst or catalyst) can be introduced.

The relative duration for the filling/emptying of the solids, based on the duration of a full period, is advantageously between 0% and 100%, preferably between 0% and 50%, more preferably between 0% and 25%.

Advantageously, the filling/emptying of the solids runs synchronously in time with the steps of "holding" and/or "heating" and/or "expulsion" and/or "production" and/or "purging".

Step: Expulsion

Advantageously, the expulsion of the gas holdup takes place in each cycle. The expulsion step is optionally executed at the start and/or at the end of the production phase. If the expulsion takes place at the start of the production phase, the flow through the reactor is advantageously in the same flow direction as during the regeneration phase. If the expulsion takes place at the end of the production phase, the flow through the reactor is advantageously in the same flow direction as during the production phase.

The gas in the feed may comprise hydrogen, carbon monoxide, carbon dioxide, steam, nitrogen, argon or a mixture of these gases.

The feed temperature of the gas stream during the expulsion step is advantageously −150 to 750° C., preferably −75 to 600° C., more preferably 4 to 400° C., especially 20 to 250° C.

During the expulsion step, the gas stream advantageously has a flow rate in the production zone of 0.001 to 20 m/s, preferably of 0.01 to 10 m/s, further preferably of 0.05 to 5 m/s, especially of 0.1 to 2 m/s.

The volume of the gas supplied to the reactor during the expulsion step is advantageously one to one thousand times, preferably twice to one hundred times, more preferably five to ten times, the reactor volume. The gas volume corresponds here to the volume at the inlet pressure and at the feed temperature during the expulsion step.

The relative duration of the expulsion step, based on the duration of a full period, is advantageously between 0 and 10%.

The solid packing in the production zone, analogously to the production step and to the purge step, may have different states of fluidization during the expulsion step if the flow through it is in the same flow direction as during the production phase: advantageously a moving bed or a fluidized bed, preferably a fluidized bed.

When the flow through the solid packing in the production zone during the expulsion step is in the same flow direction as during the regeneration phase, it may be a moving bed.

Advantageously, the expulsion step proceeds synchronously in time with the steps of "storing" (identical flow direction of the reactant) or "release" (reverse flow direction of the reactant).

Step: Holding

The holding step is optionally executed at the start and/or at the end of the production phase. This advantageously interrupts the flow of gas through the production bed.

The relative duration of the holding step, based on the duration of a full period, is advantageously between 0 and 50%, preferably between 0 and 10%.

Advantageously, the holding step runs synchronously in time with the "release" step in the heat recovery zone and/or with the "expulsion/introduction" step in the production zone.

General Details:

In the design of the cycles, the following rules among others should advantageously be followed:

1. The ratio between the heat capacity of the gases that flow through the production bed during the regeneration phase and the heat capacity of the gases that flow through the production bed during the production phase is advantageously between 0.5 and 2, preferably between 0.7 and 1.5, more preferably between 0.9 and 1.1.

2. The ratio of the heat capacities of the gas streams that flow through the reactor during the production step and during the purge step must correspond roughly to the following rule:

$$\frac{C_{purge}}{C_{prod}} = \frac{X_{eq}}{\Delta T_{eff}} \cdot |\Delta T_{ad}|$$

where $$C_{purge} \left[\frac{J}{kg}\right]:$$

heat capacity of the gas during purge step $$C_{prod} \left[\frac{J}{kg}\right]:$$

heat capacity of the gas during production step $X_{eq}$ [%]: equilibrium conversion of the reactant achievable at the required preheating temperature during the production phase.

$\Delta T_{eff}$ [K]: effective temperature rise within the reaction zone. $\Delta T_{eff}$ corresponds to the differential between the required preheating temperature and the onset temperature of the endothermic reaction.

$|\Delta T_{ad}|$ [K]: absolute magnitude of the adiabatic change in temperature in the endothermic reaction (for definition see http://elib.uni-stuttgart.de/bitstream/11682/2350/1/docu_FU.pdf page 31).

The pressure in the reactor can optionally be varied during the individual phases of the cycles. The following variants are advantageous: (i) production phase at high pressure of advantageously 2 to 60 bar, preferably 3 to 50 bar, more preferably 5 to 40 bar, especially 10 to 30 bar, and regeneration phase at low pressure of advantageously ambient pressure to pressure of the production phase. In this case we refer to a pressure swing mode. When the production phase and the regeneration phase have different pressures, the production gas and the regeneration gas are advantageously guided in two separate circuits. (ii) Production phase and regeneration phase at high pressure of advantageously 2 to 60 bar, preferably 3 to 50 bar, more preferably 5 to 40 bar, especially 10 to 30 bar. In a pressure swing mode, the solids (carrier, solid-state catalyst or catalyst) are advantageously introduced at low pressure, especially at from advantageously 1 to 10 bar absolute, preferably 1 to 6 bar absolute, more preferably 1 to 4 bar absolute.

The reactor can advantageously be run up from the cold state by supplying the reactor with an inert gas, for example nitrogen or argon, and periodically reversing the flow direction through the reactor at time intervals of 1 minute to 100 minutes, preferably of 2 minutes to 50 minutes, more preferably of 5 minutes to 20 minutes. At the same time, advantageously, the heat input in the heating zone is activated. The running-up phase advantageously takes between 1 and 100 cycles, preferably between 5 and 20 cycles. After this running-up phase, the process is switched to the mode of operation as intended.

Reactor

The present invention also includes a structured reactor comprising three zones, a production zone containing a packing of solid particles, a heating zone and a heat recovery zone containing a fixed bed, for example a random packing of shaped bodies or a structured packing composed of monoliths or profiled plates, wherein the packing of solid particles and the fixed bed consist of different materials and solid particles can be introduced and discharged during reactor operation.

The heating zone may be disposed in the connection above the production zone and the heat recovery zone (FIG. 1). In this design, the heating zone is directly accessible from above. As a result, the required apparatuses for the metered addition and distribution of the sidestream during the heat input step can be installed via one end face of the reactor.

Between the heating zone and the heat recovery zone, a hot gas filter, composed of silicon carbide for example, may advantageously be installed. In this filter, solid particles entrained with the product stream, e.g. carbon particles, are advantageously retained and incinerated or gasified. During the regeneration phase, the filter is advantageously backflushed and hence its reliable functioning is ensured.

In addition to the random particle bed that forms the production bed, the production zone may advantageously be equipped with a heat storage means composed of monoliths. The ratio of the channel width of the monoliths to the grain size of the particles is advantageously between 10 and 100, preferably between 20 and 50. The monoliths may advantageously consist of thermally stable ceramic or of carbon. The monoliths may advantageously fill the production zone over the entire length or in zones. The channel width of the monoliths is advantageously between 2 to 100 mm, preferably 5 to 50 mm.

The production zone, heating zone and heat recovery zone may advantageously be arranged vertically in a line (FIG. 2).

Dimensioning

The reactor of the invention may be configured, for example, as a shaft reactor. Each shaft advantageously has a length of 0.5 m to 50 m, preferably of 1 m to 20 m, more preferably of 2 m to 20 m. The flow cross section of the shafts is advantageously between 0.0005 m² and 100 m², preferably between 0.005 m² and 50 m². The production bed advantageously takes up more than 50%, preferably more than 70%, of the total height of the shaft in the production zone. The regenerator bed takes up more than 50%, preferably more than 70%, of the total height of the shaft in the heat recovery zone.

The shaft reactor advantageously has refractory lining and thermal insulation.

The table shows the performance indices of different process variants for the case of methane pyrolysis. Specific advantages and disadvantages derive therefrom.

| | | | Velocity in the feed $m_{std}$/s | | | |
|---|---|---|---|---|---|---|
| | Hydro- | | Production bed | | Regenerator bed | |
| Process variant | gen yield | Thermal efficiency | Pro- duction | Purging | Storage | Release |
| Two-step with hot gas feeding according to FIG. 3 | 76% | 88% | 0.42 | — | 1.68 | 1.70 |
| Three-step operation with internal heat generation according to FIG. 4 | 86% | >97% | 0.36 | 2.39 | 2.43 | 2.29 |
| Three-step operation with internal heat generation according to FIG. 5 | 86% | >97% | 0.36 | 0.80 | 0.81 | 1.53 |
| Two-step operation with internal heat generation according to FIG. 6 | 76% | 88% | 0.42 | — | 0.89 | 1.70 |

Modes of Operation:

The reactor of the invention can advantageously be operated in two-step operation with hot gas feeding (FIG. 3b):

| | Production phase 1st step | Regeneration phase 2nd step |
|---|---|---|
| Production bed | Production | Heating |
| Heating zone | Heat input | Idling |
| Regenerator bed | Storage | Release |

The term "two-step operation" relates to the number of steps in the production phase within a cycle, not taking account of the steps of expulsion, holding and introducing and emptying solids.

In the first step, production advantageously takes place in the production bed, while there is a heat input in parallel in the heating zone and storage takes place in the regenerator bed. In the second step, the heating advantageously takes place in the production bed, while the release takes place in the regenerator bed.

Advantages and disadvantages of two-step operation are as follows:
Simple configuration for the performance of the process of the invention.
Moderate temperature gradients.
Full heat recovery not achievable.
A gaseous heat carrier heated up to the level of the preheating temperature has to be fed into the heating zone at two to five times the volume flow rate of the reactant stream.
Dilution of the product stream by the gaseous heat carrier.

Alternatively, the reactor of the invention can advantageously be operated in three-step operation with heat generation in the heating zone (FIG. 4b and FIG. 5b):

| | Production phase | | Regeneration phase |
|---|---|---|---|
| | 1st step | 2nd step | 3rd step |
| Production bed | Production | Purging | Heating |
| Heating zone | Idling | Heat input | Idling |
| Regenerator bed | Storage | Storage | Release |

The term "three-step operation" relates to the number of steps in the production zone within a cycle, not taking account of the steps of expulsion, holding and introducing and emptying solids.

In the first step, production advantageously takes place in the production bed, while storage takes place in the regenerator bed. In the second step, the purging advantageously takes place in the production bed, while there is a heat input in the heating zone and storage takes place in the regenerator bed. In the third step, the heating advantageously takes place in the production bed, while the release takes place in the regenerator bed.

Advantages and Disadvantages:
Simple configuration for the performance of the process of the invention.
Full heat recovery achievable.
The product stream can be obtained with high concentrations/purity without dilution by gas from the purge step.
Complex process control: three steps per cycle.
The gas throughputs of different size in the three steps complicate the dimensioning of the reactor in terms of flow.
Temperature gradients in the environment of the heating zone.

Variants of the Reactor Structure

Heaters may advantageously be installed in the production zone. These apparatuses may, for example, be gas-fired radiant tubes, electrical heaters and/or electrodes that pass electrical current through the solid packing. Heating surfaces may also advantageously be installed in the regenerator bed.

Alternatively, multiple side feeds may be installed along the heat recovery zone. This variant is shown in FIG. 6. The number of side feeds is advantageously ascertained by the following rule:

$$n_{inj} = 1 + \text{int}\left(\frac{X_{eq}}{\Delta T_{eff}} \cdot |\Delta T_{ad}|\right)$$

where
$n_{inj}$: number of side feeds
int: function: integer part of a real number
$X_{eq}$ [%]: equilibrium conversion of the reactant achievable at the required preheating temperature during the production phase.
$\Delta T_{eff}$ [K]: effective rise in temperature within the reaction zone. $\Delta T_{eff}$ corresponds to the difference between the required preheating temperature and the onset temperature of the endothermic reaction.
$|\Delta T_{ad}|$[K]: absolute magnitude of the adiabatic change in temperature of the endothermic reaction (for definition see http://elib.uni-stuttgart.de/bitstream/11682/2350/1/docu_FU.pdf page 31).

For the determination of the position of the feeds, a length scale is crucial, which can be referred to in an illustrative manner as "movement interval of a thermal front". The movement interval of a thermal front is determined by the following rule:

$$L_{th} = \frac{(\dot{m} \cdot c_p)_g}{(\rho \cdot c)_{fxb}} \cdot \Delta t$$

where
$L_{th}$[M]: movement interval of a thermal front.

$$\dot{m}_g \left[\frac{kg}{m^2 \cdot s}\right]:$$

superficial velocity of the gas flow in the heat recovery zone.

$$c_{p,g} \left[\frac{J}{kg \cdot K}\right]:$$

specific heat capacity of the gas on entry into the heat recovery zone.

$$\rho_{fxb} \left[\frac{kg}{m^3}\right]:$$

density of the solid packing in the heat recovery zone.

$$c_{fxb} \left[\frac{J}{kg \cdot K}\right]:$$

specific head capacity of the solid packing in the heat recovery zone.
Δt [s]: duration of the relevant time interval (in general, duration of the storage step within the cycle).

The positions of the side feeds are advantageously fixed by the following rules: (i) the distance of the first side feed from the upper end of the heat recovery zone advantageously corresponds to the movement interval of the thermal front during the storage step, (ii) the distance between successive side feeds advantageously corresponds to the movement interval of the thermal front during the storage step.

This variant of the reactor of the invention can advantageously be operated in two-step operation with heat generation in the heating zone (FIG. 6b):

|  | Production phase 1st step | Regeneration phase 2nd step |
| --- | --- | --- |
| Production bed | Production | Heating |
| Heating zones | Heat input | Idling |
| Regenerator bed | Storage | Release |

Advantages and Disadvantages:
  Complete utilization of the heat capacity of the regenerator bed possible with moderate gas flows.
  Relatively low contamination/dilution of the product stream by the combustion gases from the heat input.
  Embedding of one or more heating zones into the regenerator bed is complex in terms of construction and material technology.
  Full heat recovery not achievable.
  Temperature gradients in the environment of the heating zones.

Advantageously, the reactor of the invention can also be equipped with two production beds (FIG. 7). The production beds are advantageously connected to the regenerator bed at the upper end. Each of the two production beds can advantageously be connected separately to an inlet or outlet in the periphery of the process. The streams from the two production beds are advantageously combined at the inlet into the heating zone. The gas temperature at the inlet into the heating zone is advantageously between the onset temperature of the endothermic reaction and the required preheating temperature.

The reactor of the invention can advantageously be operated in four-step operation with heat generation in the heating zone (FIG. 7b):

|  | Production phase | | Regeneration phase | |
| --- | --- | --- | --- | --- |
|  | 1st step | 2nd step | 3rd step | 4th step |
| 1st production bed | Production | Holding | Purging | Heating |
| 2nd production bed | Purging | Heating | Production | Holding |
| Heating zone | Heat input | Idling | Heat input | Idling |
| Regenerator bed | Storage | Release | Storage | Release |

The term "four-step operation" relates to the number of steps in the production zone within a cycle, not taking account of the expulsion steps.

In the first step, production advantageously takes place in the first production bed, while purging takes place in the second production bed. In parallel, the heat input takes place in the heating zone and the storage in the regenerator bed.

In the second step, the holding advantageously takes place in the first production bed, while the heating takes place in the second production bed. In parallel, the release takes place in the regenerator bed.

In the third step, the purging advantageously takes place in the first production bed, while the production takes place in the second production bed. In parallel, the heat input takes place in the heating zone and the storage in the regenerator bed.

In the fourth step, the heating advantageously takes place in the first production bed, while the holding takes place in the second production bed. In parallel, the release takes place in the regenerator bed.

Advantages and Disadvantages:
  Full heat recovery achievable.
  Holding step without flow through the production bed can be utilized for the filling and emptying of solids.
  Relatively low contamination/dilution of the product stream by the combustion gases from the heat input.
  Moderate temperature gradients.
  Complex process control: four steps per cycle.
  Complex apparatuses: three vessels and the corresponding periphery (metering and shutoff units for gas and solids) required in a reactor.

Combination of Multiple Reactors

The cyclic mode of operation entails batchwise production. In order to achieve continuous production, it is advantageously possible to connect two or more reactors of the invention in parallel. Advantageously, the production step is conducted in at least one reactor.

With parallel connection of two reactors of the invention having one production bed, one heating zone and one regenerator bed each in two-step operation, the following steps advantageously take place (FIG. 3c and FIG. 6c):

|  |  | 1st step | 2nd step |
|---|---|---|---|
| 1st reactor | Production bed | Production | Heating |
|  | Heating zone | Heat input |  |
|  | Regenerator bed | Storage | Release |
| 2nd reactor | Production bed | Heating | Production |
|  | Heating zone |  | Heat input |
|  | Regenerator bed | Release | Storage | not taking account of the steps of expulsion, holding and introducing and emptying solids.

In the first step, the production advantageously takes place in the production bed of the first reactor, while the heat input takes place in the heating zone of the first reactor and the storage in the regenerator bed of the first reactor. In parallel, the heating advantageously takes place in the production bed in the second reactor, while the heat release takes place in the regenerator bed of the second reactor.

In the second step, the heating advantageously takes place in the production bed of the first reactor, while the release takes place in the regenerator bed of the first reactor. In parallel, in the second reactor, the production advantageously takes place in the production bed, while the heat input takes place in the heating zone of the second reactor and the release in the regenerator bed of the second reactor.

With parallel connection of two reactors of the invention having one production bed, one heating zone and one regenerator bed each in three-step operation, the following steps advantageously take place (see FIG. 4c):

|  |  | 1st step | 2nd step | 3rd step | 4th step |
|---|---|---|---|---|---|
| 1st reactor | Production bed | Production | | Purging | Heating |
|  | Heating zone | Idling | Idling | Heat input | Idling |
|  | Regenerator bed | Storage | Storage | Storage | Release |
| 2nd reactor | Production bed | Purging | Heating | Production | |
|  | Heating zone | Heat input | Idling | Idling | Idling |
|  | Regenerator bed | Storage | Release | Storage | Storage | not taking account of the steps of expulsion, holding and introducing and emptying solids.

In the first step, the production advantageously takes place in the production bed of the first reactor, while the storage takes place in the regenerator bed of the first reactor. In parallel, in the second reactor, the purging advantageously takes place in the production bed, while the heat input takes place in the heating zone and the storage takes place in the regenerator bed of the second reactor.

In the second step, the production advantageously takes place in the production bed of the first reactor, while the storage takes place in the regenerator bed of the first reactor. In parallel, in the second reactor, the heating advantageously takes place in the production bed, while the release takes place in the regenerator bed of the second reactor.

In the third step, the purging advantageously takes place in the production bed of the first reactor, while the heat input takes place in the heating zone and the storage takes place in the regenerator bed of the first reactor. In parallel, in the second reactor, the production advantageously takes place in the production bed, while the storage takes place in the regenerator bed of the second reactor.

In the fourth phase, the heating advantageously takes place in the production bed of the first reactor, while the release takes place in the regenerator bed of the first reactor. In parallel, in the second reactor, the production advantageously takes place in the production bed, while the storage takes place in the regenerator bed of the second reactor.

With parallel connection of three reactors of the invention having one production bed, one heating zone and one regenerator bed each in three-step operation, the following steps advantageously take place (see FIG. 5c):

|  |  | 1st step | 2nd step | 3rd step |
|---|---|---|---|---|
| 1st reactor | Production bed | Production | Purging | Heating |
|  | Heating zone | Idling | Heat input | Idling |
|  | Regenerator bed | Storage | Storage | Release |
| 2nd reactor | Production bed | Purging | Heating | Production |
|  | Heating zone | Heat input | Idling | Idling |
|  | Regenerator bed | Storage | Release | Storage |
| 3rd reactor | Production bed | Heating | Production | Purging |
|  | Heating zone | Idling | Idling | Heat input |
|  | Regenerator bed | Release | Storage | Storage | not taking account of the steps of expulsion, holding and introducing and emptying solids.

In the first step, the production advantageously takes place in the production bed of the first reactor, while the storage takes place in the regenerator bed of the first reactor. In parallel, in the second reactor, the purging advantageously takes place in the production bed, while the heat input takes place in the heating zone and the storage takes place in the regenerator bed of the second reactor. In parallel, in the third reactor, the heating advantageously takes place in the production bed, while the release takes place in the regenerator bed of the third reactor.

In the second step, the purging advantageously takes place in the production bed of the first reactor, while the heat input takes place in the heating zone and the storage takes place in the regenerator bed of the first reactor. In parallel, in the second reactor, the heating advantageously takes place in the production bed, while the release takes place in the regenerator bed of the second reactor. In parallel, in the third reactor, the production advantageously takes place in the production bed, while the storage takes place in the regenerator bed of the third reactor.

In the third step, the heating advantageously takes place in the production bed of the first reactor, while the release takes place in the regenerator bed of the first reactor. In parallel, in the second reactor, the production advantageously takes place in the production bed, while the storage takes place in the regenerator bed of the second reactor. In parallel, in the third reactor, the purging advantageously takes place in the production bed, while the heat input takes place in the heating zone and the storage takes place in the regenerator bed of the third reactor.

With parallel connection of two reactors of the invention having two production beds, one heating zone and one regenerator bed each in four-step operation, the following steps advantageously take place (see FIG. 7c):

|  |  | 1st step | 2nd step | 3rd step | 4th step |
|---|---|---|---|---|---|
| 1st reactor | 1st production bed | Production | Holding | Purging | Heating |
|  | 2nd production bed | Purging | Heating | Production | Holding |
|  | Heating zone | Heat input | Idling | Heat input | Idling |
|  | Regenerator bed | Storage | Release | Storage | Release |
| 2nd reactor | 1st production bed | Heating | Production | Holding | Purging |
|  | 2nd production bed | Holding | Purging | Heating | Production |
|  | Heating zone | Idling | Heat input | Idling | Heat input |
|  | Regenerator bed | Release | Storage | Release | Storage | not taking account of the expulsion steps.

In the first step, the production advantageously takes place in the first production bed of the first reactor and the purging in the second production bed of the first reactor, while the heat input takes place in the heating zone of the first reactor and the storage takes place in the regenerator bed of the first reactor. In parallel, in the second reactor, the heating advantageously takes place in the first production bed and the holding step takes place in the second production bed of the second reactor, while the release takes place in the regenerator bed of the second reactor.

In the second step, the holding step advantageously takes place in the first production bed of the first reactor and the heating takes place in the second production bed of the first reactor, while the release takes place in the regenerator bed of the first reactor. In parallel, in the second reactor, the production advantageously takes place in the first production bed and the purging takes place in the second production bed of the second reactor, while the storage takes place in the heating zone of the second reactor and in the regenerator bed of the second reactor.

In the third step, the purging advantageously takes place in the first production bed of the first reactor and the production takes place in the second production bed of the first reactor, while the heat input takes place in the heating zone of the first reactor and the storage takes place in the regenerator bed of the first reactor. In parallel, in the second reactor, the holding step advantageously takes place in the first production bed and the heating takes place in the second production bed of the second reactor, while the release takes place in the regenerator bed of the second reactor.

In the fourth step, the heating advantageously takes place in the first production bed of the first reactor and the holding step takes place in the second production bed of the first reactor, while the release takes place in the regenerator bed of the first reactor. In parallel, in the second reactor, the purging advantageously takes place in the first production bed and the production takes place in the second production bed of the second reactor, while the heat input takes place in the heating zone of the second reactor and the storage takes place in the regenerator bed of the second reactor.

Advantages

The present invention solves the following feasibility problems with reactor concepts considered to date for methane pyrolysis: (i) fouling of the heating surfaces by coke deposits in the case of indirect heating, (ii) forced coupling of the solid particle flow rate to the demands of heat integration and/or heat demand, (iii) heat loss as a result of unequal adjustment of the heat capacity flows between the production phase and the regeneration phase and consequently asynchronous temperature fronts, (v) yield loss as a result of the reverse reaction of the hydrogen during the cooling in the heat recovery zone, (vi) handling of hot solids and (vii) contamination by the flue gases from combustion.

Moreover, the present invention mitigates the greatest cost drivers (see estimate below) in the concepts considered in the prior art in that it (i) eliminates the need for heat-transferring walls in the region of the production zone, (ii) the gates for solid material for the supply of the solid particle stream into the reactor can be designed for ambient pressure and (iii) the process offers full heat integration.

The process heat required in the present invention is generated by combustion in the heating zone of the reactor. The complex heat transfer surfaces for indirect coupling of the process heat at high temperature are dispensed with. Thus, the flow rate of solids that is guided through the reactor is no longer rigidly coupled to the demands of heat integration. More particularly, the flow rate of solids can correspond specifically to the production rate of the solid product, such that the holdup in the production zone remains constant. The gaseous product stream is separated from the carbon at the highest temperature level; thus, yield losses resulting from a reverse reaction are ruled out.

The reactor may be designed as a shaft apparatus (with one, two or three shafts) without any structuring of the cross section. The simple geometry permits refractory lining and thermal insulation of the reactor chamber. Thus, the pressure-rated reactor shell can be effectively protected from the high temperatures of the reaction media.

By virtue of the optional installation of multiple heat sources in the heating zone, for example burners, plasma generators or resistance heaters, the concept of the invention offers the option of switching flexibly and in a cost-optimized manner between different energy carriers. It is thus possible to implement hybrid heating of the process, as described, for example, in WO 2014/090914.

Estimate of the Costs:

| Cost element | Proportion of total capital costs | Saving potential |
|---|---|---|
| Heating | 25% to 60% | 80%* |
| $H_2$ dedusting | 15% to 25% | 80%** |
| Solids handling | 10% to 15% | 50%*** |

*saving potential
(i) compared to processes with indirect heating: by dispensing with heat transfer walls in the high-temperature region
(ii) compared to processes with electrical heating: dispensing with electrodes/electrical resistors in the high-temperature region
**saving potential compared to fluidized bed processes:
The reaction regime in a bed at rest suppresses soot formation. The regenerator bed functions as a regeneratable filter for dust particles. It is thus possible to dispense with an external filtration stage.
***The cyclical process has two advantages:
(i) The loading and emptying of the reactor can be conducted in a bed through which there is no flow.
(ii) Optionally, the cyclical process can be operated in pressure swing mode: production at high pressure and regeneration at low pressure. In this case, the pressure balancing in the gates for solid material can be dispensed with.
(iii) The flow rate of solids which is guided through the production zone is about 30% of the flow rate of solids required in moving bed reactors, in which the heat recovery is based on the countercurrent flow between the gaseous process stream and the solid process stream.

FIGURES

Labels for FIGS. 1 and 2

1: production bed
2: regenerator bed

3: heating zone
4: mixing/combustion chamber
5: introduction of the carrier
6: emptying of the solid product
7: hot gas filter
8: additional heating in the production bed
9: additional heating in the regenerator bed
10: phase separator/dedusting FIG. 1 shows a schematic diagram of the reactor of the invention with one production bed and one regenerator bed in parallel arrangement.

FIG. 2 shows a schematic diagram of the reactor of the invention with one production bed and one regenerator bed in a vertical arrangement.

Labels for FIG. 3

1: production bed
2: regenerator bed
3: heating zone
4: mixing/combustion chamber
5: introduction of the carrier
6: emptying of the solid product
7: hydrocarbon-containing feed stream
8: product gas exit stream
9: regeneration gas exit stream
10: regeneration gas feed stream
13: oxygen-containing feed stream
14: fuel-containing feed stream FIG. 3a shows a schematic diagram of the process of the invention with two reactors of identical design, each with one production bed, one heating zone and one regenerator bed, where the heat input is accomplished by combustion of a fuel in an external combustion chamber.

Figure 1:
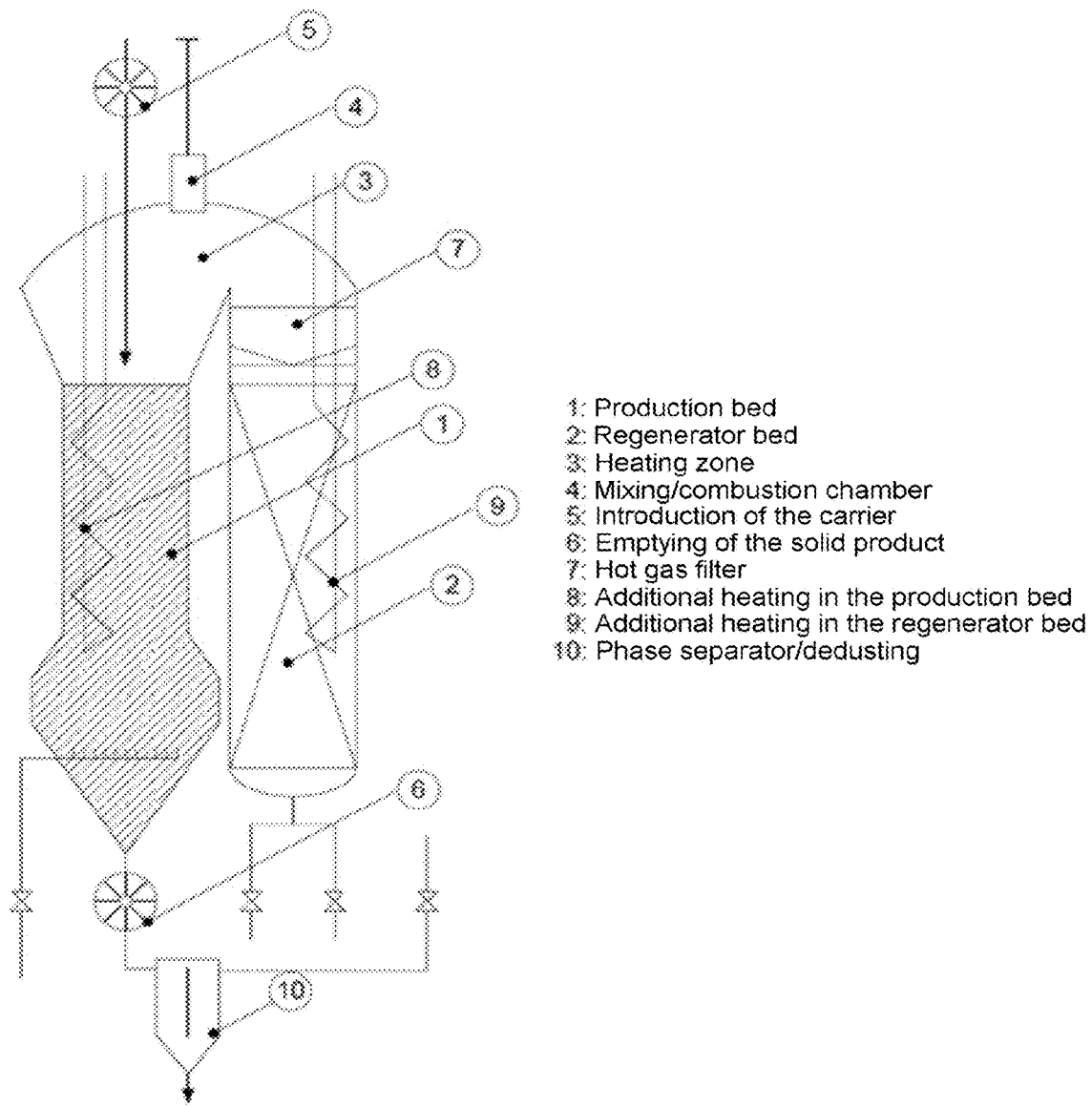
Figure 2:
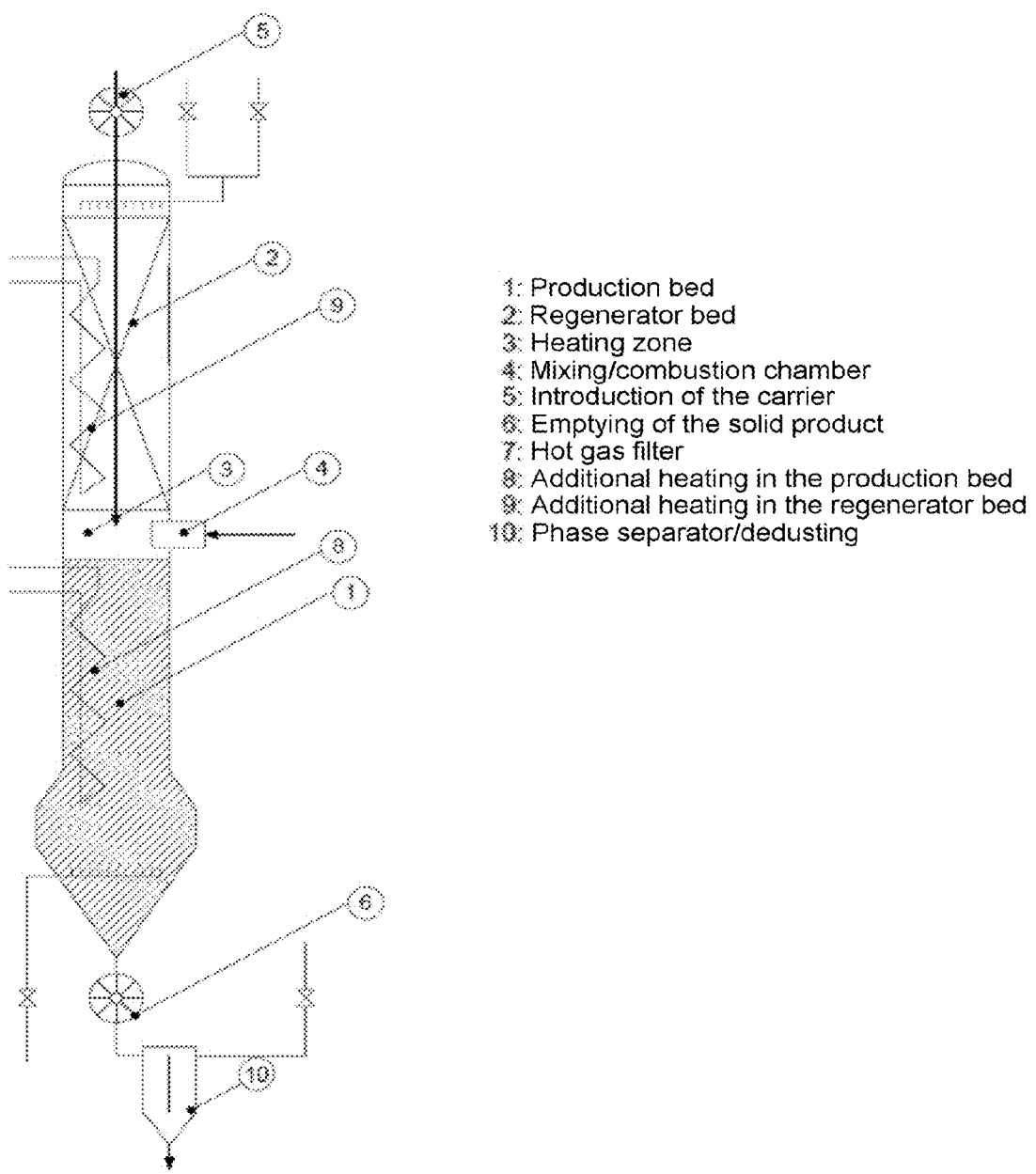
Figure 3A:
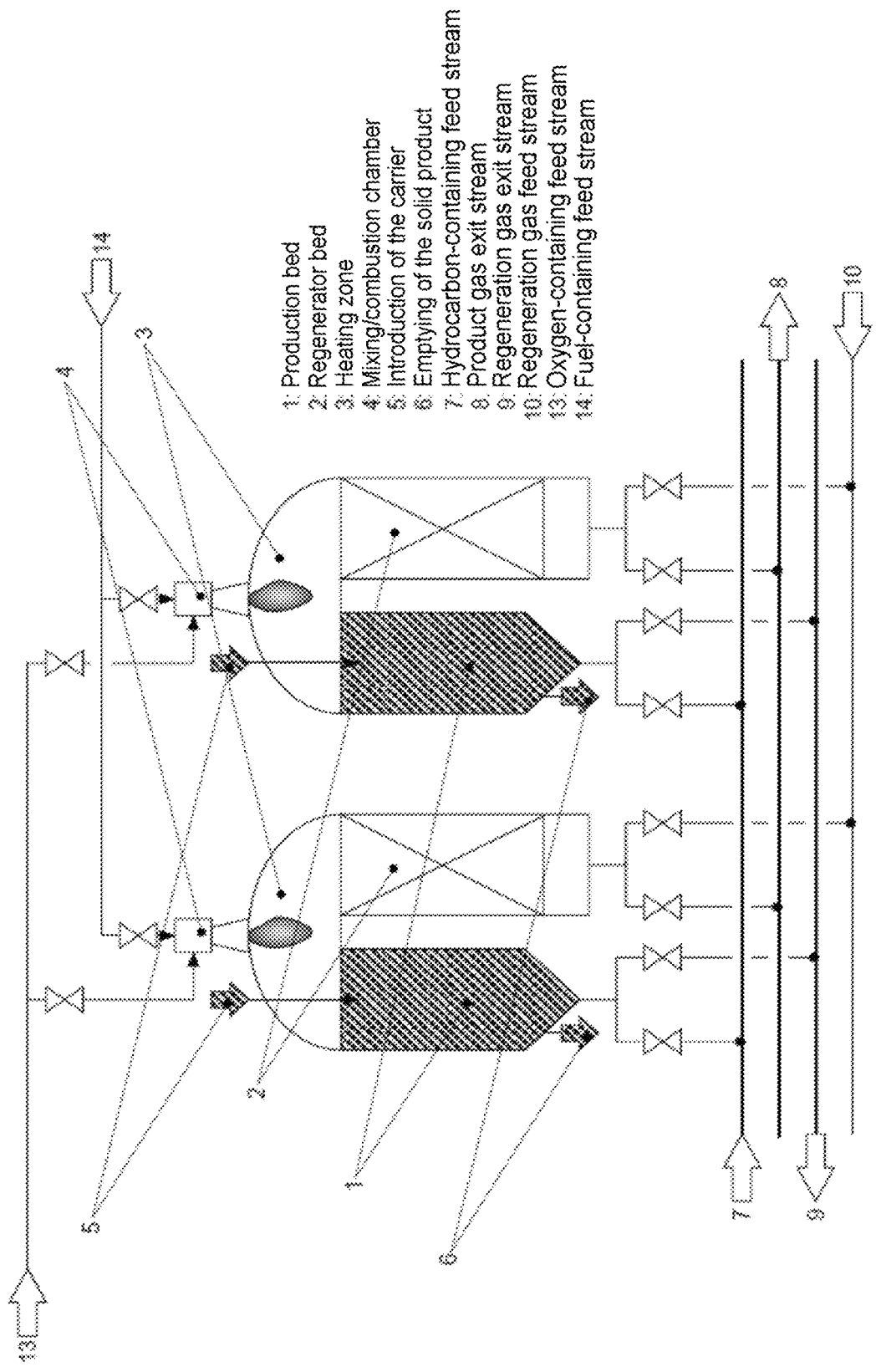
FIG. 3b shows the flow diagram in the process of the invention through a cycle with two main steps in the production bed.
FIG. 3c shows the flow diagram of a quasi-continuous production in the process of the invention in a configuration with two reactors of identical design.
Figure 3:
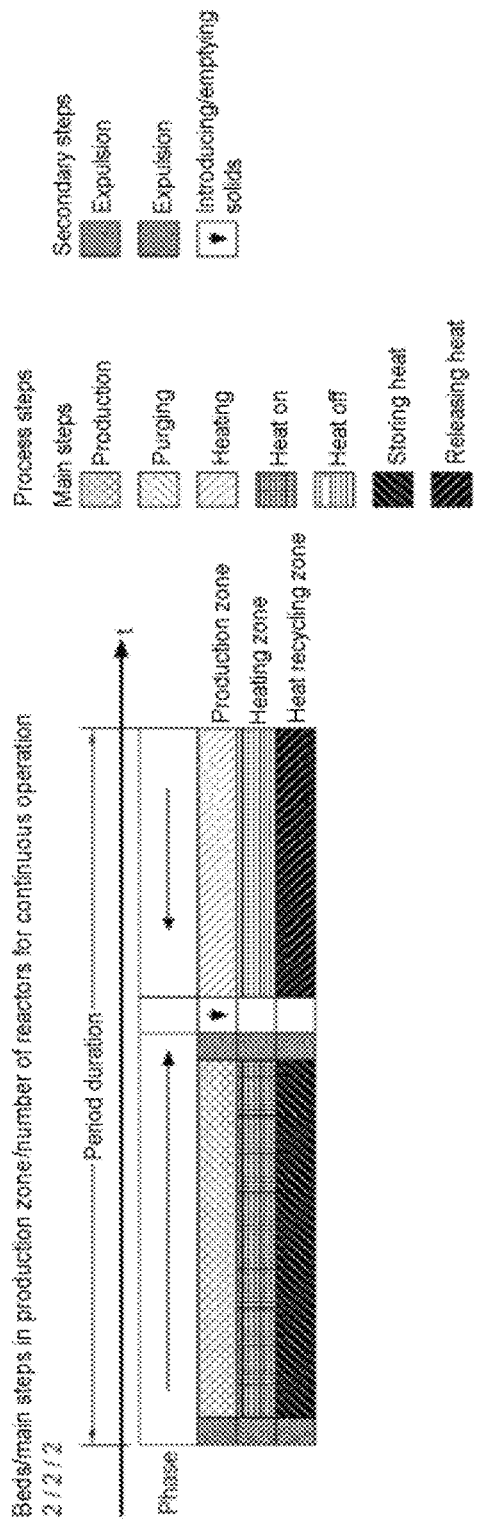
Figure 3:
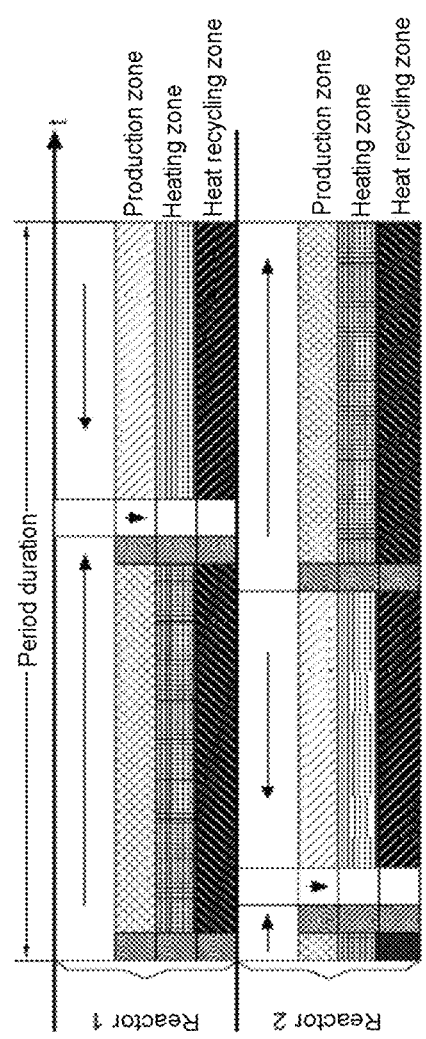
Figure 4:
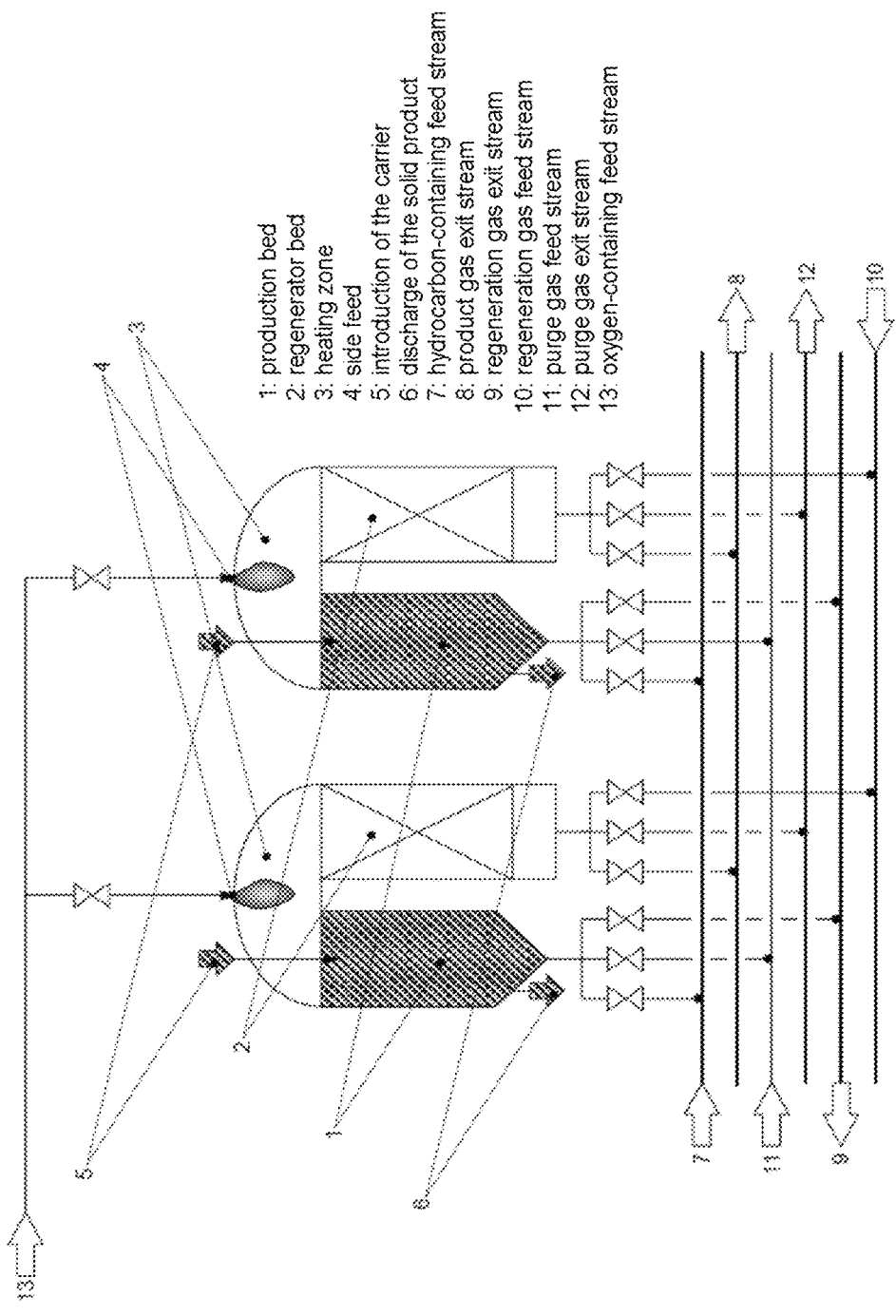
Figure 4:
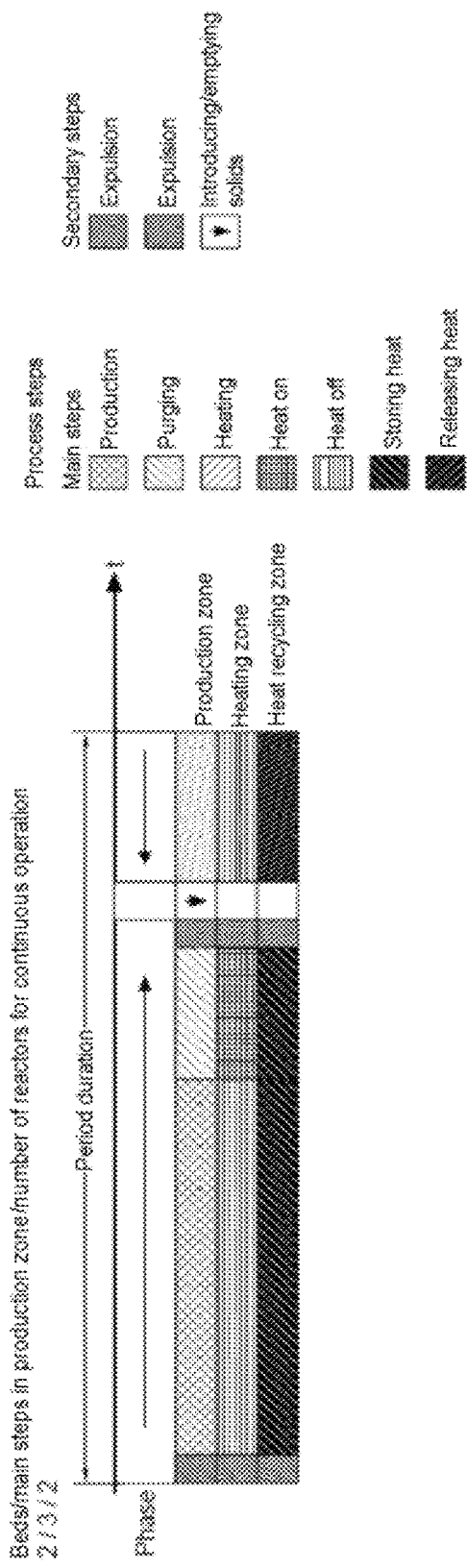
Figure 4:
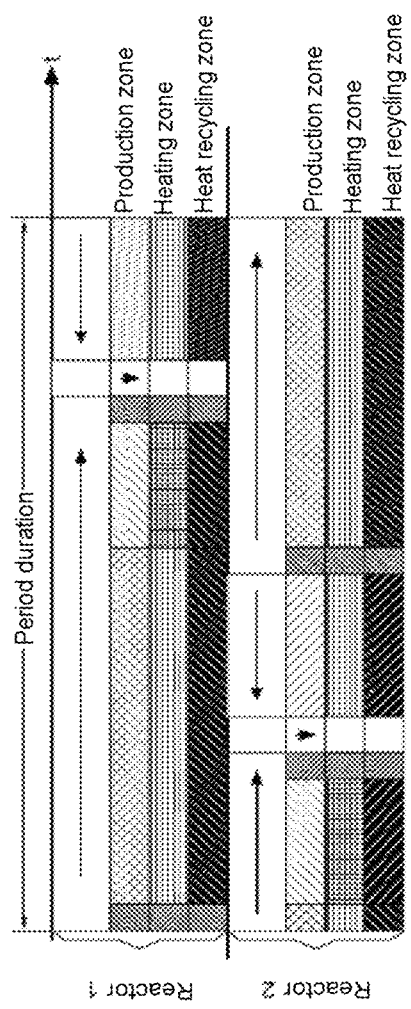

Labels for FIG. 4

1: production bed
2: regenerator bed
3: heating zone
4: side feed
5: introduction of the carrier
6: discharge of the solid product
7: hydrocarbon-containing feed stream
8: product gas exit stream
9: regeneration gas exit stream
10: regeneration gas feed stream
11: purge gas feed stream
12: purge gas exit stream
13: oxygen-containing feed stream FIG. 4a shows a schematic diagram of the process of the invention with two reactors of identical design, each with one production bed, one heating zone and one regenerator bed, where the heat input is accomplished by side feeding of an oxidizer into the heating zone.

FIG. 4b shows the flow diagram in the process of the invention through a cycle with three main steps in the production bed.

FIG. 4c shows the flow diagram of a quasi-continuous production in the process of the invention in a configuration with two reactors of identical design.

Figure 5:
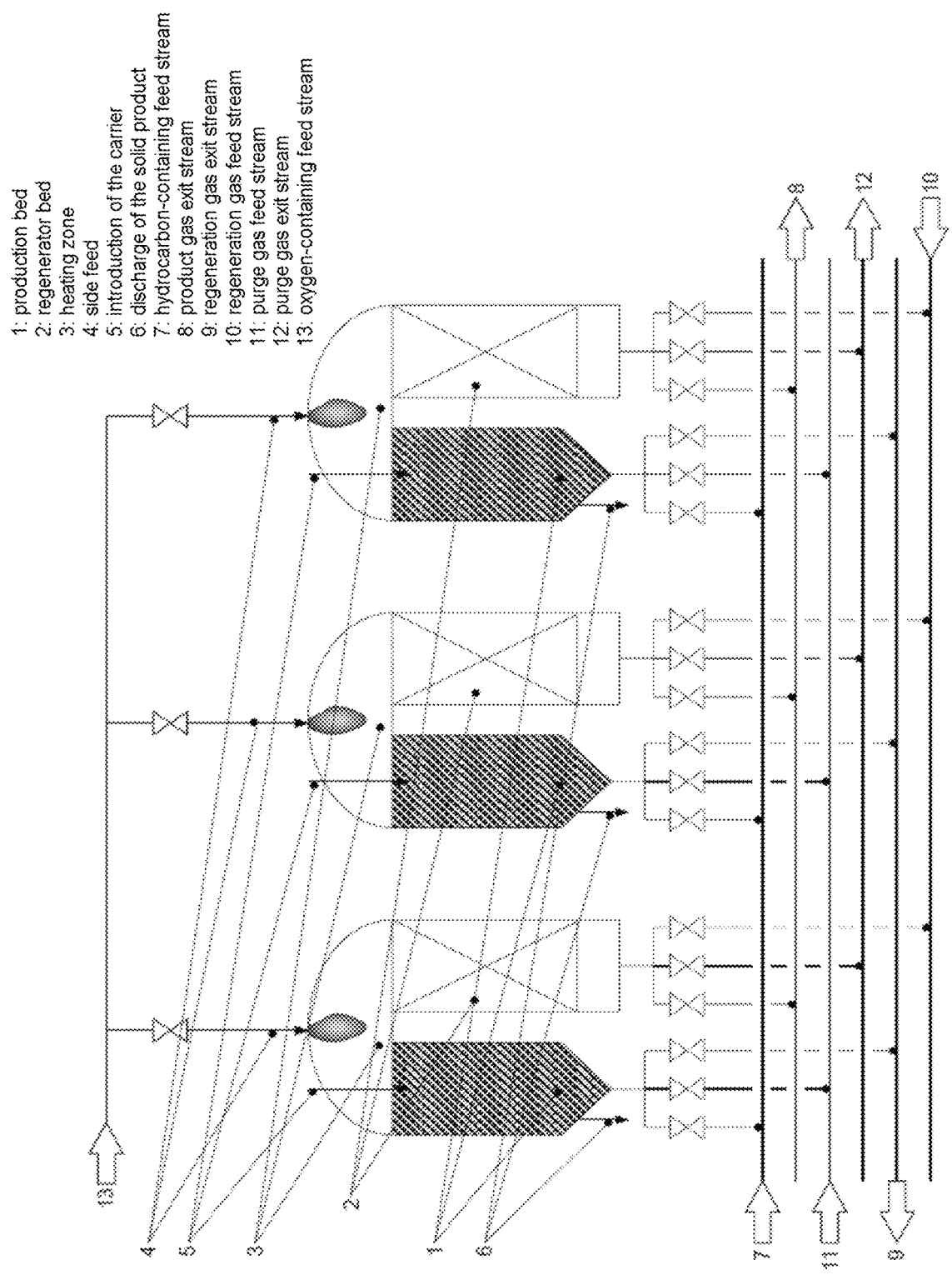
Figure 5:
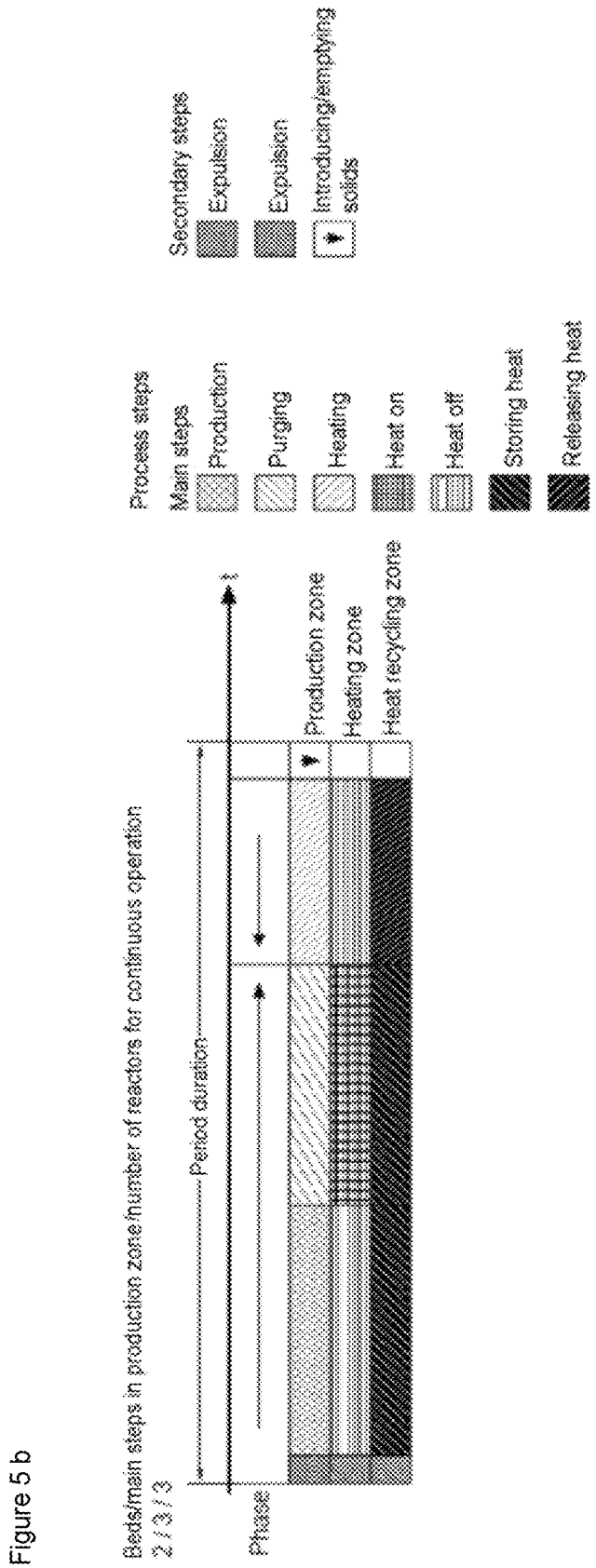
Figure 5:
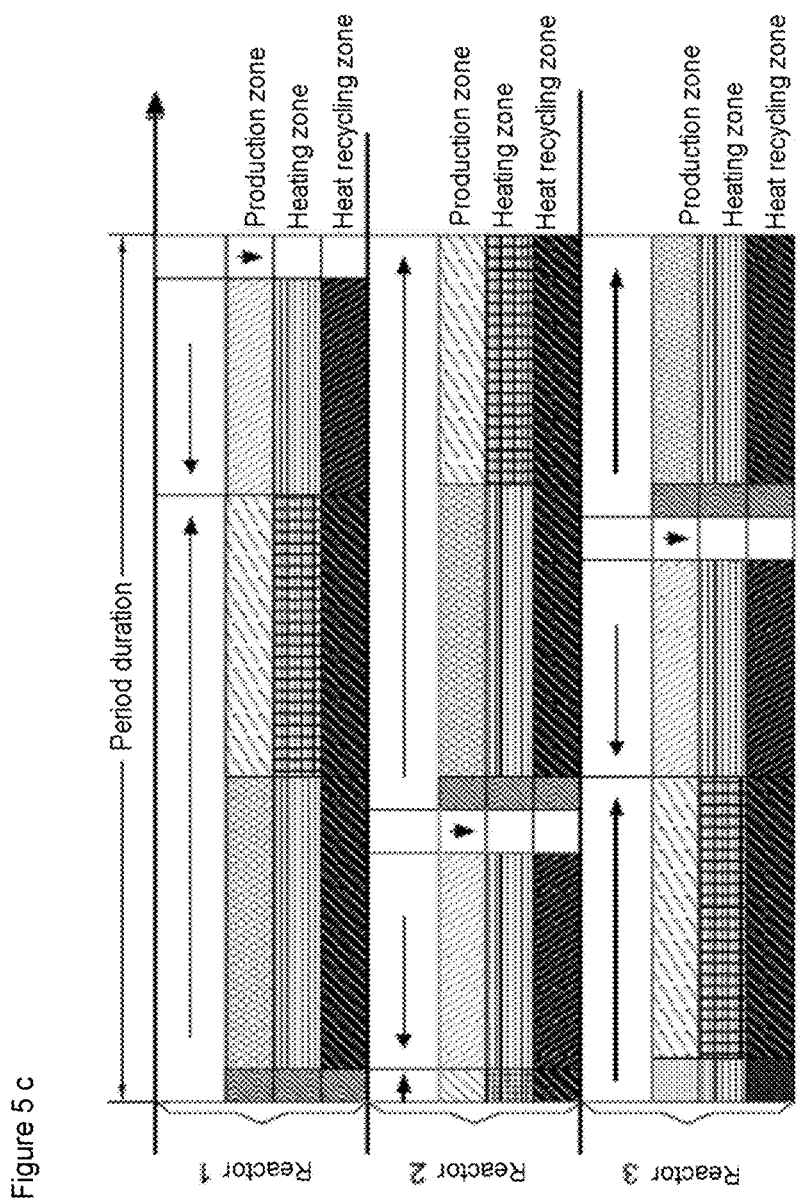

Labels for FIG. 5

1: production bed
2: regenerator bed
3: heating zone
4: side feed
5: introduction of the carrier
6: discharge of the solid product
7: hydrocarbon-containing feed stream
8: product gas exit stream
9: regeneration gas exit stream
10: regeneration gas feed stream
11: purge gas feed stream
12: purge gas exit stream
13: oxygen-containing feed stream FIG. 5a shows a schematic diagram of the process of the invention with three reactors of identical design, each with one production bed, one heating zone and one regenerator bed, where the heat input is accomplished by side feeding of an oxidizer into the heating zone.

FIG. 5b shows the flow diagram in the process of the invention through a cycle with three main steps in the production bed.

FIG. 5c shows the flow diagram of a quasi-continuous production in the process of the invention in a configuration with three reactors of identical design.

Figure 6:
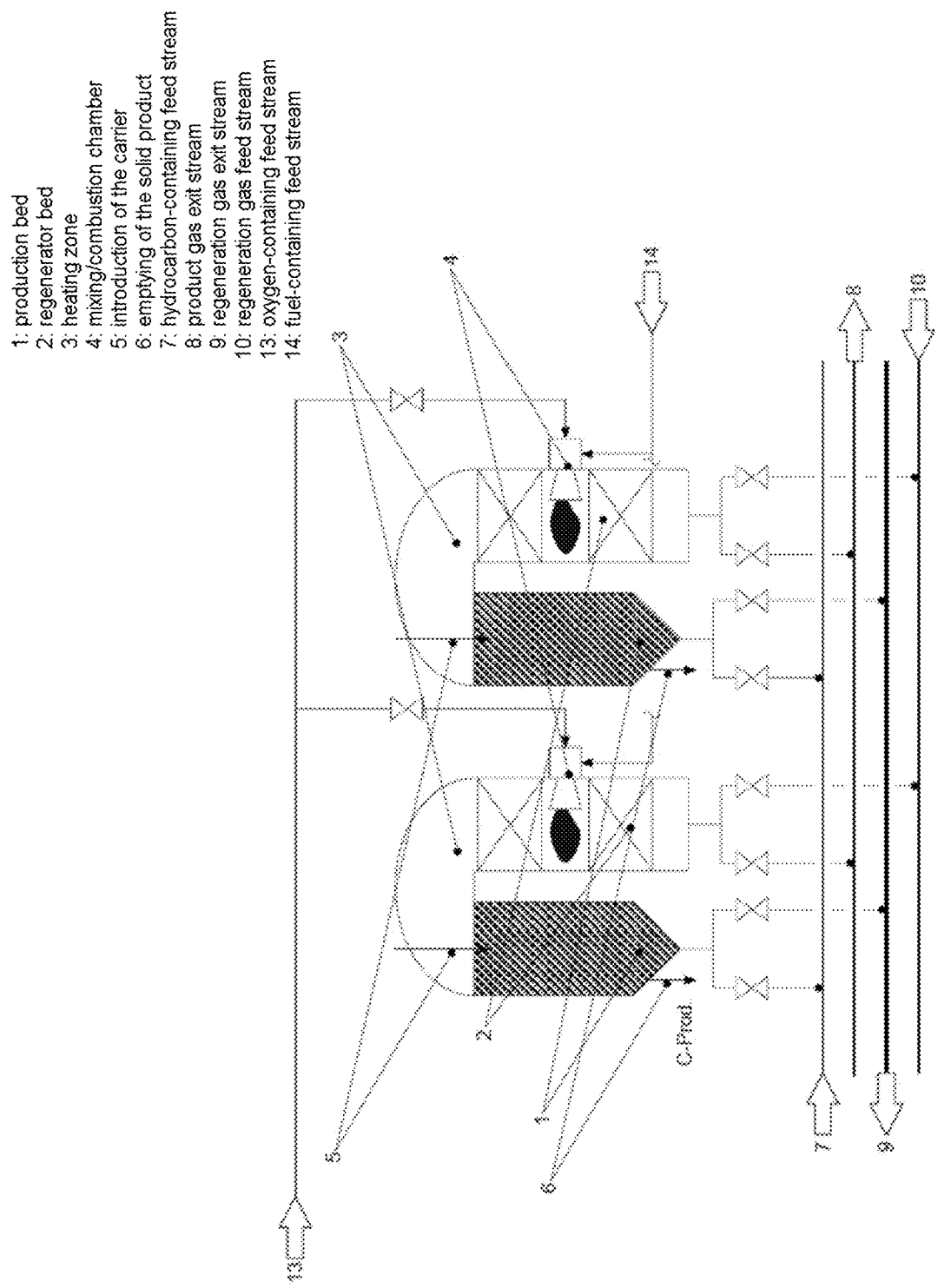

Labels for FIG. 6

1: production bed
2: regenerator bed
3: heating zone
4: mixing/combustion chamber
5: introduction of the carrier
6: emptying of the solid product
7: hydrocarbon-containing feed stream
8: product gas exit stream
9: regeneration gas exit stream
10: regeneration gas feed stream
13: oxygen-containing feed stream
14: fuel-containing feed stream FIG. 6a shows a schematic diagram of the process of the invention with two reactors of identical design, each with one production bed, one heating zone and one regenerator bed, where the heating zone is integrated in the heat recovery zone and the heat input can be accomplished by combustion of a fuel in an external combustion chamber or by side feeding of an oxidizer into the heating zone.

FIG. 6b shows the flow diagram in the process of the invention through a cycle with two main steps in the production bed.

FIG. 6c shows the flow diagram of a quasi-continuous production in the process of the invention in a configuration with two reactors of identical design.

Figure 7:
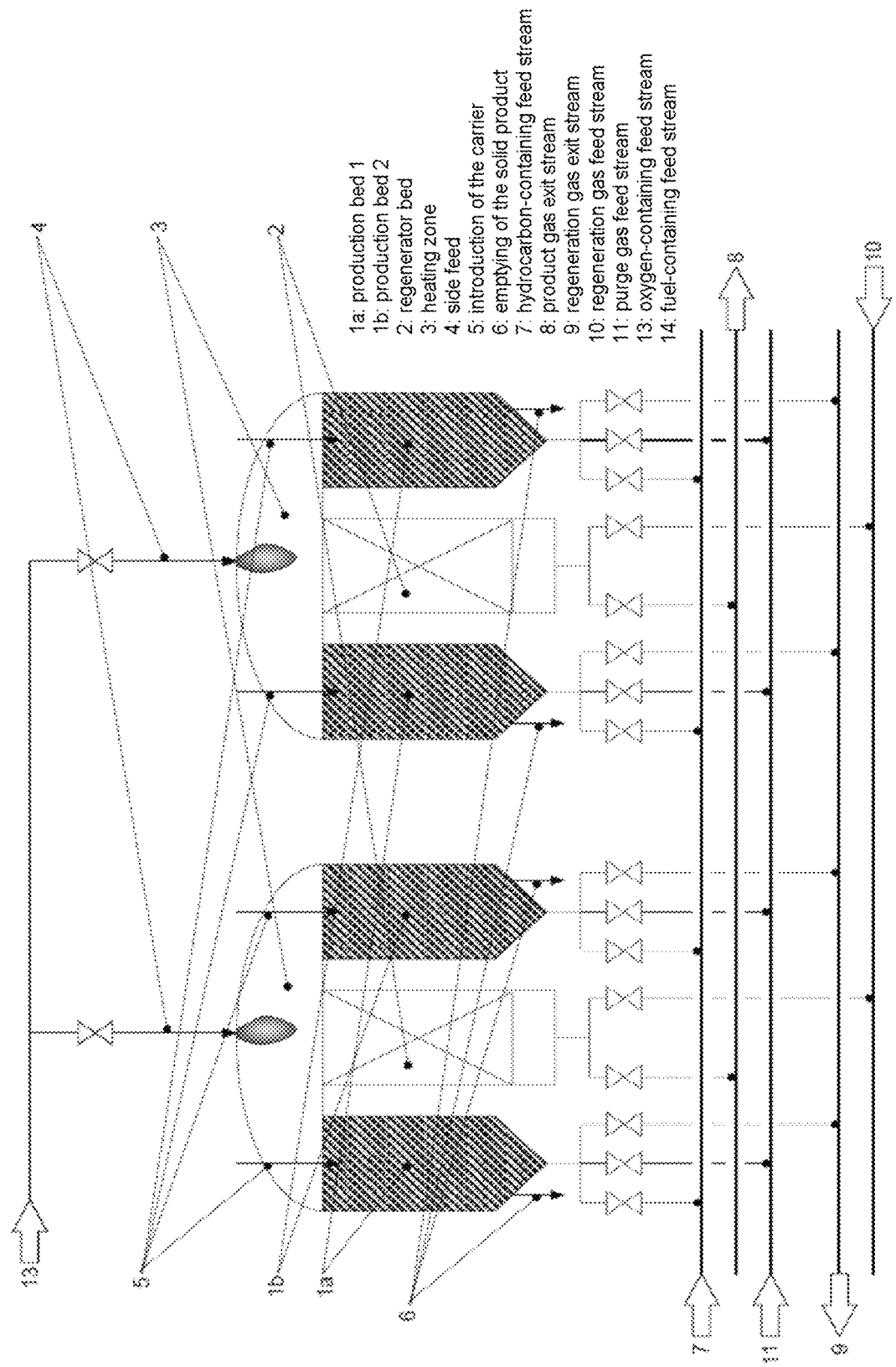
Figure 7:
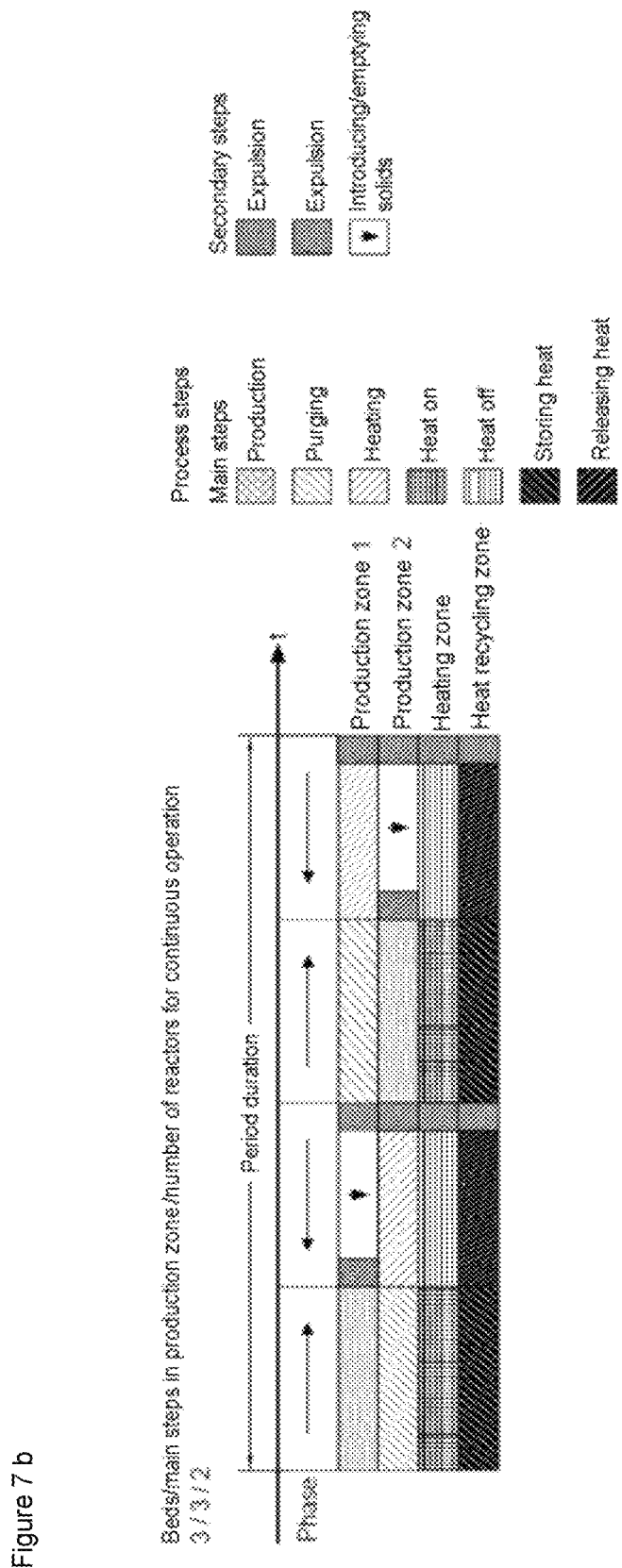

Labels for FIG. 7

1a: production bed 1
1b: production bed 2
2: regenerator bed
3: heating zone
4: side feed
5: introduction of the carrier
6: emptying of the solid product
7: hydrocarbon-containing feed stream
8: product gas exit stream
9: regeneration gas exit stream 10: regeneration gas feed stream
11: purge gas feed stream
13: oxygen-containing feed stream
14: fuel-containing feed stream FIG. 7a shows a schematic diagram of the process of the invention with two reactors of identical design, each with two production beds, one heating zone and one regenerator bed, where the heat input is accomplished by side feeding of an oxidizer into the heating zone. In this configuration, two reactors of identical design are required for continuous production.

FIG. 7b shows the flow diagram in the process of the invention through a cycle with three main steps in the production beds.

Figure 7C:
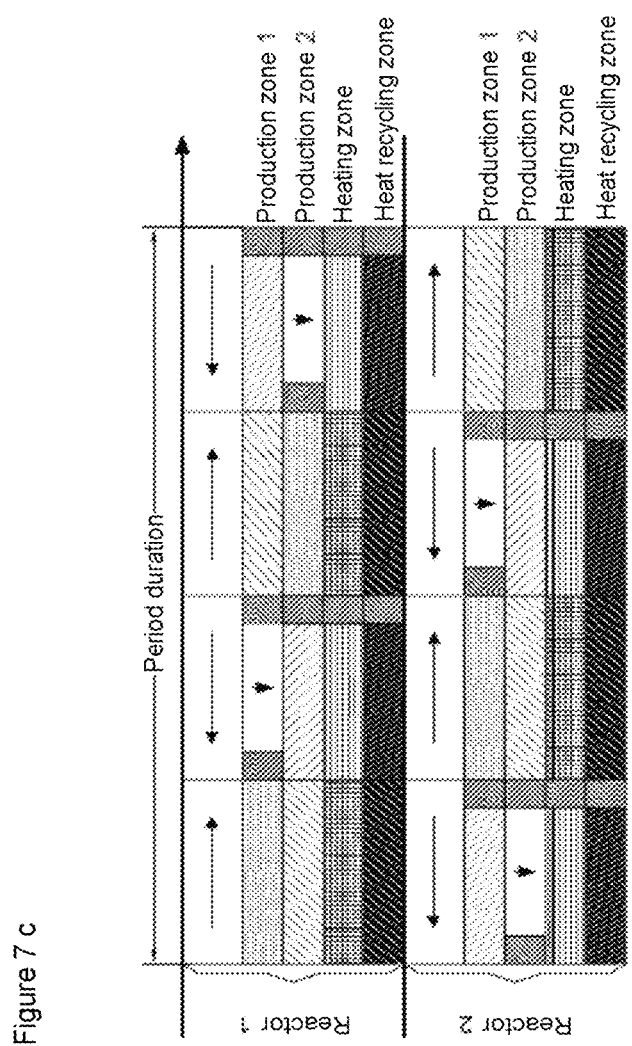

FIG. 7c shows the flow diagram of a quasi-continuous production in the process of the invention in a configuration with two reactors of identical design.

Figure 8:
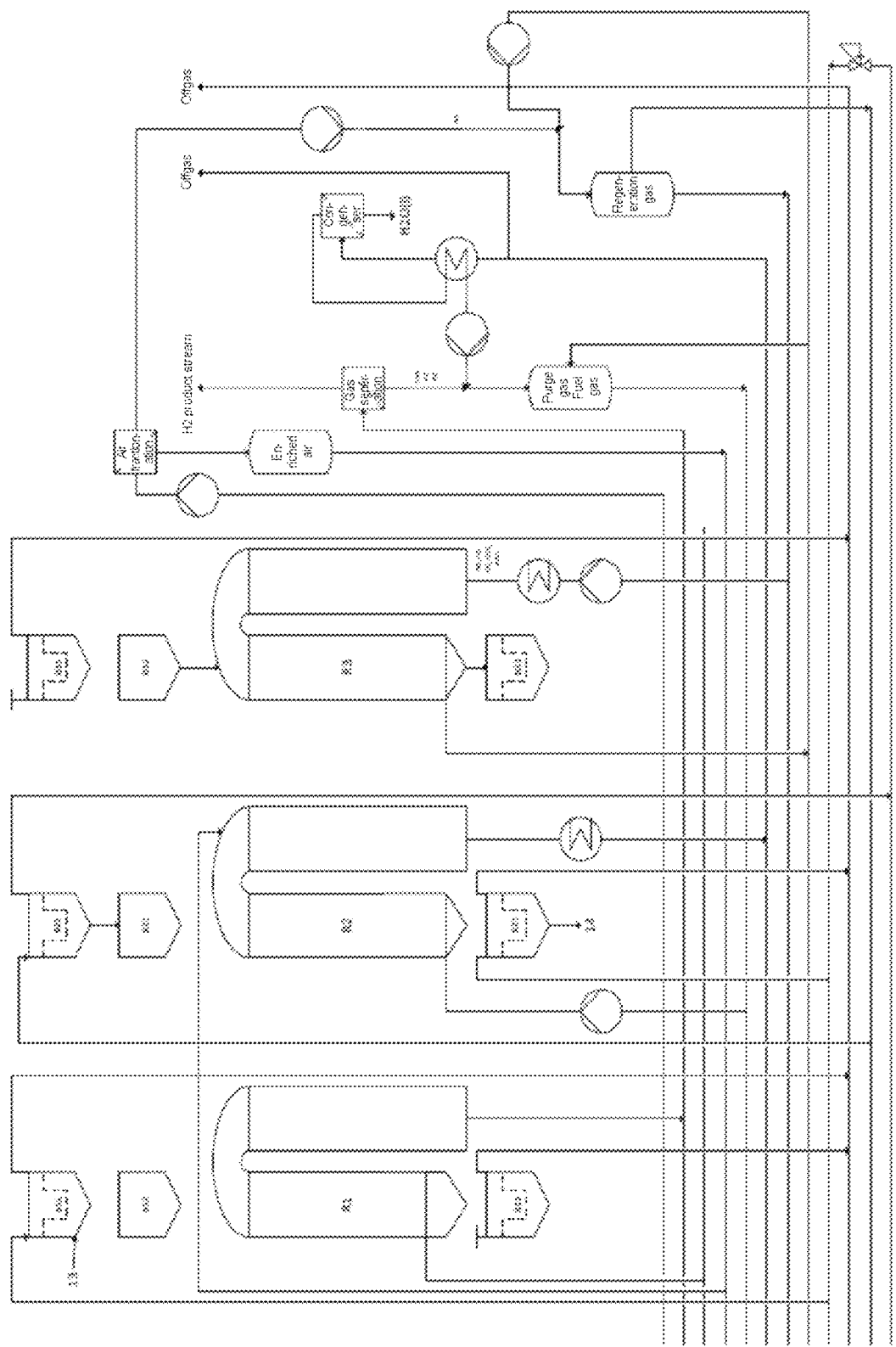

FIG. 8 shows, by way of example, the process flow diagram of an integrated, quasi-continuous process of the invention. In this process, natural gas (strand 3) and air (strand 1) are introduced as gaseous feed streams. The natural gas is the feedstock for the production of the hydrogen and pyrolysis carbon target products. The air is divided into two substreams. One substream (strand 4) is oxygen-rich and is guided as oxidizer into the heating zone. The second substream is nitrogen-rich and is used as main stream during the regeneration phase (strand 7) and as purge gas for the buffer, reservoir and discharge vessels (strand 9, strand 11) for the solid process streams. The process comprises three reactors that are synchronized in a cycle. Only the active conduits are shown in each case. In the reactor R1, the production bed is in the production step, the heating zone is idling and the regenerator bed is in the "storing heat" step. The buffer vessel for the solid carrier B11 is filled. The discharge vessel B13 is decompressed. In the reactor R2, the production bed is in the "purging" step, the heating zone in the "heat input" step and the regenerator bed in the "storing heat" step. The buffer vessel B21 is pressurized with nitrogen to the level of the process pressure and the solid carrier is transferred from the buffer vessel B21 into the reservoir vessel B22. The discharge vessel B23 is emptied. In the reactor R3, the production bed is in the "heating" step, the heating zone at idling and the regenerator bed in the "releasing heat" step. The buffer vessel B31 is decompressed. The solid carrier is introduced from the reservoir vessel B32 into the production zone of the reactor R3. At the same time, the solid reaction product from the production zone of the reactor R3 is transferred into the discharge vessel B33. In the periphery of the reactors, the following process steps are present: in the air fractionation stage, the feed air is separated into an oxygen-rich fraction and a nitrogen-rich fraction. In the gas separation stage, the gaseous crude product is separated into a hydrogen-rich product stream and a retentate stream. The retentate is recycled into the process as main stream for the purge step. The gas from the purge step is partly dried in a condenser and recycled into the process. The nitrogen-rich stream is at the level of the process pressure (strand 11 and strand 12) and is available as purge gas for pressure compensation with the environment (strand 9 and strand 10). The process is designed for an annual production capacity of 720 000 m³ (STP) of hydrogen. The production bed and the regenerator bed have a cross section of 44 m² and a bed height of 6 m. The production bed is filled with a carbon carrier having an average grain size of 3 mm and a bed density of 800 kg/m³.

The regenerator bed consists of particles of alumina having an average grain size of 3 mm. The process pressure of the feed streams is 10 $bar_{abs}$. The feed temperature of the feed streams is 200° C. The preheating temperature is 1800° C. The cycle duration is 5400 s. Within one cycle, the production step, the purging step and the heating step each last for 1800 s. The stream profile shows, in tabular form, the streams in the individual strands averaged over the duration of a step.

Example

Stream Profile

| | Molar flow rates [kmol/h] | | | | | | | |
|---|---|---|---|---|---|---|---|---|
| Stream | C | CH4 | CO | CO2 | H2 | H2O | N2 | O2 |
| 1 | 0 | 0 | 0 | 0 | 0 | 0 | 1602 | 400 |
| 2 | 0 | 23 | 0 | 0 | 4455 | 0 | 133 | 0 |
| 3 | 0 | 2250 | 0 | 0 | 0 | 0 | 133 | 0 |
| 4 | 0 | 0 | 0 | 0 | 0 | 0 | 128 | 400 |
| 5 | 0 | 23 | 45 | 1 | 755 | 6 | 6633 | 0 |
| 6 | 0 | 0 | 57 | 11 | 33 | 774 | 6761 | 0 |
| 7 | 0 | 0 | 0 | 0 | 0 | 0 | 11207 | 0 |
| 8 | 0 | 0 | 0 | 0 | 0 | 0 | 11207 | 0 |
| 9 | 0 | 0 | 0 | 0 | 0 | 0 | 11207 | 0 |
| 10 | 0 | 0 | 0 | 0 | 0 | 0 | 11207 | 0 |
| 11 | 0 | 0 | 0 | 0 | 0 | 0 | 11207 | 0 |
| 12 | 0 | 0 | 0 | 0 | 0 | 0 | 11207 | 0 |
| 13 | 1125 | 0 | 0 | 0 | 0 | 0 | 0 | 0 |
| 14 | 3353 | 0 | 0 | 0 | 0 | 0 | 0 | 0 |

The invention claimed is:

1. A process for conducting an endothermic gas phase or gas-solid reactions, the process comprising:
   conducting an endothermic reaction of a reactant-containing gas in a production step in a first reactor zone, a production zone, which is at least partly filled with solid particles, where the solid particles are in the form of a fixed bed, of a moving bed and in sections, or in the form of a fluidized bed,
   drawing off a product-containing gas stream from the production zone, wherein the product-containing gas stream comprises one or more of carbon, hydrogen, olefins, propylene, butene, styrene, benzene, synthesis gas, CO, or HCN,
   guiding the product-containing gas stream through a second reactor zone, a heat recovery zone, which at least partly comprises a fixed bed, where the heat from the product-containing gas stream is stored in the fixed bed,
   in a subsequent purge step, guiding an inert purge gas through the production zone and the heat recovery zone in the same flow direction as that of the product-containing gas stream,
   wherein the purge gas comprises at least one gas selected from the group consisting of hydrogen, carbon monoxide, carbon dioxide, steam, nitrogen, argon, and mixtures thereof,
   in a heating zone disposed between the production zone and the heat recovery zone, introducing the heat required for the endothermic reaction into the product-containing gas stream and into the purge stream or into the purge stream,
   and then, in a regeneration phase, passing a gas through the two reactor zones in a reverse flow direction compared to the flow direction of the purge gas and heating up the production zone,
   wherein the process is operated cyclically, wherein the production step takes between 20% and 60% of a period duration of the process, the purge step takes between 10% and 40% of the period duration, and the regeneration phase between 20% and 60% of the period duration.

2. The process according to claim 1, wherein the heat required for the endothermic reaction is introduced into the purge stream.

3. The process according to claim 1 wherein, during the regeneration phase, heat input in the heating zone has a heating output per unit volume of the heating zone of less than 100 kW/m$^3$.

4. The process according to claim 1, wherein a rate of descent of a solid stream in the production zone, averaged over a period, is in the range from 0 m/h to 50 m/h.

5. The process according to claim 1, wherein a specific interfacial area between the solid particles in the production zone and a gas phase and/or the fixed bed in the heat recovery zone and a gas phase is greater than 50 in$^2$/m$^3$.

6. The process according to claim 1, wherein the solid particles in the production zone are a catalyst for an endothermic gas phase reaction, a solid-state catalyst for an endothermic gas-solid reaction, and/or the product of an endothermic reaction, and wherein the fixed bed in the heat recovery zone is chemically inert in relation to a reverse reaction of the endothermic reaction.

7. The process according to claim 1, wherein the ratio between the heat capacity of the gases that flow through the production bed during the regeneration phase and the heat capacity of the gases that flow through the production bed during the production phase is between 0.5 and 2.

8. The process according to claim 1, wherein the heat required for the endothermic reaction is supplied by combustion of a fuel gas with the aid of an oxygen-rich gas in the heating zone, where the fuel gas is present in a main flow leaving the production zone during the production step or during the purge step and the fuel gas enters the heating zone at temperatures of 350° C. to 1200° C.

9. The process according to claim 1, wherein the loading and unloading of the production zone with solid particles takes place while no reactant-containing gas is flowing through the production zone.

10. The process according to claim 1, wherein the reactant-containing gas is introduced in a reactant-containing stream with a flow rate in the production zone of 0.001 to 20 m/s.

11. The process according to claim 1, wherein the endothermic gas phase or gas-solid reactions that are conducted are the following processes:
preparation of hydrogen, of synthesis gas, of styrene, propene, hutene and/or benzene, of acetylene, of carbon monoxide, and of hydrogen cyanide.

12. The process according to claim 11, wherein the endothermic gas phase or gas-solid reactions that are conducted are one of the following processes: preparation of synthesis gas, of styrene, propene, butene and/or benzene, of acetylene, of carbon monoxide, or of hydrogen cyanide.

13. The process according to claim 1, wherein the product-containing gas stream comprises one or more of carbon, olefins, propylene, butene, styrene, benzene, synthesis gas, CO, or HCN.

14. A process comprising:
(a) introducing a reactant-containing gas in a flow direction into a preheated production zone and conducting an endothermic reaction in the production zone which is at least partly filled with solid particles to produce a product-containing gas stream, wherein the reactant-containing gas comprises one or more of carbon, hydrogen, olefins, propylene, butene, styrene, benzene, synthesis gas, CO, or HCN;
(b) optionally introducing heat into the product-containing gas stream in a heating zone downstream of the production zone;
(c) transferring heat from the product-containing stream from (b) to a packing of solid particles and/or structured internals in a heat recovery zone downstream of the heating zone;
(d) stopping the introduction of reactant-containing gas and purging the production zone and the heat recovery zone with an inert purge gas flowing in the same flow direction as that of the reactant-containing gas;
(e) introducing heat into the inert purge gas stream in the heating zone downstream of the production zone;
(f) stopping the introduction of inert purge gas and introducing a regeneration gas into the heat recovery zone with opposite flow direction compared to the inert purge gas;
(g) transferring heat from the solid particles and/or structured internals heated in (c) to the regeneration gas;
(h) transferring heat from the regeneration gas heated in (e) to the solid particles in the production zone; and
(i) stopping the introduction of regeneration gas into the heat recovery zone,
wherein the process is operated cyclically,
wherein the steps (a-c) takes between 20% and 60% of a period duration of the process, steps (d-e) takes between 10% and 40% of the period duration, and steps (f-i) takes between 20% and 60% of the period duration.

15. The process according to claim 14, wherein the purge gas comprises at least one selected from the group consisting of hydrogen, carbon monoxide, carbon dioxide, steam, nitrogen, argon, and mixtures thereof.

* * * * *